(12) United States Patent
Hosseini et al.

(10) Patent No.: US 11,636,599 B2
(45) Date of Patent: Apr. 25, 2023

(54) IMAGE DIAGNOSTIC SYSTEM, AND METHODS OF OPERATING THEREOF

(71) Applicant: Huron Technologies International Inc., St. Jacobs (CA)

(72) Inventors: Mahdi S. Hosseini, St. Jacobs (CA); Konstantinos N. Plataniotis, St. Jacobs (CA); Lyndon Chan, St. Jacobs (CA); Jasper Hayes, St. Jacobs (CA); Savvas Damaskinos, St. Jacobs (CA)

(73) Assignee: Huron Technologies International Inc., St. Jacobs (CA)

( * ) Notice: Subject to any disclaimer, the term of this patent is extended or adjusted under 35 U.S.C. 154(b) by 0 days.

(21) Appl. No.: 17/944,330

(22) Filed: Sep. 14, 2022

(65) Prior Publication Data
US 2023/0014668 A1  Jan. 19, 2023

Related U.S. Application Data

(63) Continuation of application No. 17/590,933, filed on Feb. 2, 2022, now Pat. No. 11,488,307, which is a
(Continued)

(51) Int. Cl.
*G06K 9/00* (2022.01)
*G06T 7/00* (2017.01)
(Continued)

(52) U.S. Cl.
CPC .......... *G06T 7/0014* (2013.01); *G06K 9/6282* (2013.01); *G16H 30/40* (2018.01);
(Continued)

(58) Field of Classification Search
CPC . G06T 2207/10056; G06T 2207/10061; G06T 2207/30024; G06T 7/10–194;
(Continued)

(56) References Cited

U.S. PATENT DOCUMENTS 10,453,197 B1 * 10/2019 Cholakkal ................. G06T 7/11
10,628,658 B2   4/2020 Bredno et al.
(Continued)

OTHER PUBLICATIONS

Strategic Plan, "The national artificial intelligence research and development strategic plan," National Science and Technology Council, Networking and Information Technology Research and Development Subcommittee, Oct. 13, 2016, USA.
(Continued)

*Primary Examiner* — Atiba O Fitzpatrick
(74) *Attorney, Agent, or Firm* — Bereskin & Parr LLP/S.E.N.C.R.L., s.r.l.

(57) ABSTRACT

Various image diagnostic systems, and methods of operating thereof, are disclosed herein. Example embodiments relate to operating the image diagnostic system to identify one or more tissue types within an image patch according to a hierarchical histological taxonomy, identifying an image patch associated with normal tissue, generating a pixel-level segmented image patch for an image patch, generating an encoded image patch for an image patch of at least one tissue, searching for one or more histopathological images, and assigning an image patch to one or more pathological cases.

36 Claims, 20 Drawing Sheets

Related U.S. Application Data continuation of application No. 16/864,389, filed on May 1, 2020, now Pat. No. 11,276,172.

(60) Provisional application No. 62/842,698, filed on May 3, 2019.

(51) Int. Cl.
   *G16H 30/40* (2018.01)
   *G06K 9/62* (2022.01)

(52) U.S. Cl.
   CPC ............ *G06T 2207/20081* (2013.01); *G06T 2207/20084* (2013.01); *G06T 2207/30024* (2013.01)

(58) Field of Classification Search
   CPC .................... G06T 2207/20021; G06T 2207/20112–20168; G06T 2207/20081; G06T 2207/20084; G06V 20/69–698; G06V 2201/04; G06V 10/25–273; G06V 20/49; G06V 20/695; G06V 40/162; G06V 20/80; G06V 10/70; G06V 10/82; G06V 10/774–7796; A61B 5/7485; G06K 9/6224; G06K 9/6256; G06K 9/6257; G06K 9/6259; G06K 9/6219; G06N 3/02–126; G06N 20/00–20; G06F 16/444
   See application file for complete search history.

(56) References Cited

U.S. PATENT DOCUMENTS

| | | | |
|---|---|---|---|
| 11,508,066 B2* | 11/2022 | Kanan | G06V 10/462 |
| 2010/0104505 A1 | 4/2010 | O'Connor | |
| 2010/0260406 A1 | 10/2010 | Sammak et al. | |
| 2014/0180977 A1 | 6/2014 | Cosatto et al. | |
| 2015/0238148 A1 | 8/2015 | Georgescu et al. | |
| 2016/0098621 A1 | 4/2016 | Tahmasebi Maraghoosh et al. | |
| 2016/0335478 A1 | 11/2016 | Bredno et al. | |
| 2017/0372117 A1 | 12/2017 | Bredno et al. | |
| 2019/0038310 A1 | 2/2019 | Bredno et al. | |
| 2019/0080450 A1 | 3/2019 | Arar et al. | |
| 2019/0080453 A1 | 3/2019 | Song et al. | |
| 2020/0134820 A1* | 4/2020 | Hendriks | G06T 7/0012 |
| 2020/0388029 A1 | 12/2020 | Singh et al. | |
| 2021/0073986 A1* | 3/2021 | Kapur | G06V 10/255 |
| 2021/0117729 A1 | 4/2021 | Bharti et al. | |
| 2021/0233236 A1* | 7/2021 | Dogdas | G06T 7/0012 |
| 2022/0051047 A1* | 2/2022 | Kanan | G06V 10/26 |
| 2022/0051403 A1* | 2/2022 | Kanan | G16H 50/20 |
| 2022/0293242 A1* | 9/2022 | Raciti | G06V 20/69 |

OTHER PUBLICATIONS

Shuchita Upadhyaya et al., "Classification based outlier detection techniques," Int J Comput Trends Technol, 2012, vol. 3, No. 2, pp. 294-298, Seventh Sense Research Group, India.

Farahani et al., "Whole slide imaging in pathology: advantages, limitations, and emerging perspectives." Pathol Lab Med Int, Jun. 11, 2015, pp. 23-33, Dovepress, UK.

Gurcan et al., "Histopathological Image Analysis: A Review", IEEE Reviews in Biomedical Engineering, vol. 2, pp. 147-171, 2009, USA.

Selvaraju et al., "Grad-CAM: Why did you say that? Visual Explanations from Deep Networks via Gradient-based Localization", CoRR, 2016.

Xie et al., "Beyond Classification: Structured Regression for Robust Cell Detection Using Convolutional Neural Network," Med Image Comput Comput Assist Interv, Nov. 18, 2015.

Ciresan et al., "Mitosis Detection in Breast Cancer Histology Images with Deep Neural Networks", IDSIA, Dalle Molle Institute for Artificial Intelligence, USI-SUPSI, Lugano, Switzerland, 2013.

Chen et al., "DCAN: Deep Contour-Aware Networks for Accurate Gland Segmentation", The Chinese University of Hong Kong, Apr. 10, 2016.

Yamashita et al. "Convolutional neural networks: an overview and application in radiology", Insights into Imaging, vol. 9, pp. 611-629, Jun. 22, 2018.

Cai et ai. "Efficient Architecture Search by Network Transformation", Proceedings of Thirty-Second AAAI Conference on Artificial Intelligence, 2018.

Wang et al., "Deep Learning for Identifying Metastatic Breast Cancer", Submitted to CAMELYON16 ISBI challenge on cancer metastasis detection in lymph node, Jun. 18, 2016, 6 pages.

Randell et al. "Diagnosis at the microscope: a workplace study of histopathology." Cognition, Technology & Work, 2012.

Mukhopadhyay et al. "Whole slide imaging versus microscopy for primary diagnosis in surgical pathology: a multi center blinded randomized noninferiority study of 1992 cases (pivotal study)", The American journal of surgical pathology, 42.1 (Jan. 2018): 39.

Evans et al. "US Food and Drug Administration Approval of Whole Slide Imaging for Primary Diagnosis: A Key Miiestonels Reached and New Questions are Raised", Archives of pathology & laboratory medicine, Nov. 2018.

Bejnordi et al. "Diagnostic assessment of deep learning algorithms for detection of lymph node metastases in women with breast cancer", Jama, 318.22 (Dec. 12, 2017): 2199-2210.

Fischer et al., "Interobserverreliability in the histopathologic diagnosis of oral pre-malignant and malignant lesions", Journal of oral pathology & medicine, 33.2 (2004): 65-70.

Plummer et al., "Histological diagnosis of precancerous lesions of the stomach: a reliability study", International journal of epidemiology, 26.4 (1997): 716-720.

International Search Report and Written Opinion of the ISA, re PCT International Application No. PCT/CA2020/050584, dated May 1, 2020, 18 pages.

* cited by examiner

| First Level | Second Level | Third Level |
|---|---|---|
| Epithelial (E) | Simple Epithelial (E.M) | Simple Squamous Epithelial (E.M.S) |
| | | Simple Cuboidal Epithelial (E.M.U) |
| | | Simple Columnar Epithelial (E.M.O) |
| | Stratified Epithelial (E.T) | Stratified Squamous Epithelial (E.T.S) |
| | | Stratified Cuboidal Epithelial (E.T.U) |
| | | Stratified Columnar Epithelial (E.T.O) |
| | | Stratified Epithelial Undifferentiated (E.T.X) |
| | Pseudostratified Epithelial (E.P) | |
| Connective Proper (C) | Dense Connective (C.D) | Dense Irregular Connective (C.D.I) |
| | | Dense Regular Connective (C.D.R) |
| | Loose Connective (C.L) | |
| | Connective Proper Undifferentiated (C.X) | |
| Blood (H) | Erythrocytes (H.E) | |
| | Leukocytes (H.K) | |
| | Lymphocytes (H.Y) | |
| | Blood Undifferentiated (H.X) | |
| Skeletal (S) | Mature Bone (S.M) | Compact Bone (S.M.C) |
| | | Spongy Bone (S.M.S) |
| | Endochondral Bone (S.E) | |
| | Cartilage (S.C) | Hyaline Cartilage (S.C.H) |
| | | Cartilage Undifferentiated (S.C.X) |
| | Marrow (S.R) | |
| Adipose (A) | White Adipose (A.W) | |
| | Brown Adipose (A.B) | |
| | Marrow Adipose (A.M) | |
| Muscular (M) | Smooth Muscle (M.M) | |
| | Skeletal Muscle (M.K) | |
| Nervous (N) | Neuropil (N.P) | |
| | Neurons (N.R) | Nerve Cell Bodies (N.R.B) |
| | | Nerve Axons (N.R.A) |
| | Neuroglial Cells (N.G) | Microglial Cells (N.G.M) |
| | | Astrocytes (N.G.A) |
| | | Oligodendrocytes (N.G.O) |
| | | Ependymal Cells (N.G.E) |
| | | Radial Glial Cells (N.G.R) |
| | | Schwann Cells (N.G.W) |
| | | Satellite Cells (N.G.T) |
| | | Neuroglial Cells Undifferentiated (N.G.X) |
| Glandular (G) | Exocrine Gland (G.O) | |
| | Endocrine Gland (G.N) | |
| | Gland Undifferentiated (G.X) | |
| Transport Vessel (T) | | |

FIG. 4

| First Level | Second Level | Third Level | |
|---|---|---|---|
| Epithelial (E) | Simple Epithelial (E.M) | Simple Squamous Epithelial (E.M.S) | |
| | | Simple Cuboidal Epithelial (E.M.U) | |
| | | Simple Columnar Epithelial (E.M.O) | |
| | Stratified Epithelial (E.T) | Stratified Squamous Epithelial (E.T.S) | |
| | | Stratified Cuboidal Epithelial (E.T.U) | |
| | | Stratified Columnar Epithelial (E.T.O) | |
| | | Stratified Epithelial Undifferentiated (E.T.X) | |
| | Pseudostratified Epithelial (E.P) | | |

FIG. 5

IMAGE DIAGNOSTIC SYSTEM, AND METHODS OF OPERATING THEREOF

CROSS-REFERENCE TO RELATED APPLICATIONS

This application is a continuation of U.S. patent application Ser. No. 17/590,933, filed on Feb. 2, 2022, which is a continuation of U.S. patent application Ser. No. 16/864,389, filed on May 1, 2020, which claims the benefit of U.S. Provisional Patent Application No. 62/842,698, filed on May 3, 2019. The complete disclosure of each of U.S. patent application Ser. No. 17/590,933, U.S. patent application Ser. No. 16/864,389 and U.S. Provisional Patent Application No. 62/842,698 is incorporated herein by reference for all purposes.

FIELD

The described embodiments relate to an image diagnostic system, and methods of operating thereof. In some example embodiments, the image diagnostic system, and methods of operating thereof, can relate to histological and histopathological images.

BACKGROUND

Pathologists typically examine tissue specimens prepared on a slide using a microscope. Often, before diagnosing the tissue specimens, pathologists screen the tissue specimens to separate normal tissue from diseased tissue. Diagnosis and classification of the diseased tissue follows thereafter. The screening process can consume a significant amount of time, which delays, and can reduce the amount of time available for, the diagnosis and classification of the specimens. Human error can also impede the screening process.

SUMMARY

The various embodiments described herein generally relate to an image diagnostic system and methods of operating thereof. The disclosed methods and systems can relate to histological images and/or histopathological images.

In accordance with an example embodiment, there is provided a system for identifying one or more tissue types within an image patch according to a hierarchical histological taxonomy. The system includes a supervised digital pathology database having a set of training image patches stored thereon; and a processor in communication with the supervised digital pathology database and operable to: access the set of training image patches stored in the supervised digital pathology database; develop a feature extractor to generate a training feature vector identifying one or more training tissue segments in each training image patch in the set of training image patches; develop a feature classifier to assign a tissue type to each training tissue segment identified in the training feature vector and to update a class confidence score for that tissue type, the tissue type being assigned according to the hierarchical histological taxonomy; apply the feature extractor to the image patch to identify one or more tissue segments within the image patch; and apply the feature classifier to assign a tissue type to the one or more tissue segments identified by the feature extractor for the image patch and to generate a confidence score for assigned tissue type within the image patch with reference to the class confidence score.

In some embodiments, the processor is operable to: develop a convolutional neural network based on the set of training image patches.

In some embodiments, the processor is operable to define an architecture of the convolutional neural network by operating a Network Architecture Search (NAS).

In some embodiments, the feature extractor is generated by applying one of local binary patterns (LBP), pre-trained convolutional neural network, local binary patterns (LBP), and Gabor filters, wavelet filters, and image differential filters.

In some embodiments, the processor is operable to: generate a feature vector identifying the one or more tissue segments of the image patch.

In some embodiments, the processor is operable to: generate a confidence score vector containing the confidence scores for each tissue type identified for the feature vector by the feature classifier.

In some embodiments, the processor is operable to: map one or more prediction models to each tissue segment within the image patch to identify the tissue type relative to the training feature vector and class confidence score for that tissue type.

In some embodiments, the processor is operable to: evaluate the confidence score generated by the feature classifier by comparing the confidence score with a confidence threshold; and generate a quality indicator indicating the confidence score satisfies the confidence threshold, and otherwise, generate the quality indicator indicating the confidence score fails to satisfy the confidence threshold.

In some embodiments, the processor is operable to construct the supervised digital pathology database by: receiving one or more image patches of normal tissue; receiving, via a labelling user interface, one or more user inputs to label each image patch with at least one tissue type according to the hierarchical histological taxonomy; storing each labelled image patch in the supervised digital pathology database.

In some embodiments, the processor is further operable to: select a subset of the training image patches stored in the supervised digital pathology database for verification; and receive, via a verification user interface, one or more user inputs to verify one or more labels associated with each training image patch of the subset the training image patches.

In some embodiments, the processor is operable to: retrieve the set of training image patches from the supervised digital pathology database.

In some embodiments, the one or more image patches are generated from at least one whole slide image of a tissue specimen.

In some embodiments, the processor is further operable to: identify one or more regions of interest in the image patch from which to generate one or more image patches; and identify the one or more tissue types in each image patch of the one or more image patches.

In some embodiments, the system includes an image patch database for storing the one or more image patches.

In accordance with an embodiment, there is provided a method for identifying one or more tissue types within an image patch according to a hierarchical histological taxonomy. The method includes operating a processor to: access a set of training image patches stored in a supervised digital pathology database; develop a feature extractor to generate a training feature vector identifying one or more training tissue segments in each training image patch in the set of training image patches; develop a feature classifier to assign a tissue type to each training tissue segment identified in the training feature vector and to update a class confidence score for that tissue type, the tissue type being assigned according to the hierarchical histological taxonomy; apply the feature extractor to the image patch to identify one or more tissue segments within the image patch; and apply the feature classifier to assign a tissue type to the one or more tissue segments identified by the feature extractor for the image patch and to generate a confidence score for assigned tissue type within the image patch with reference to the class confidence score.

In some embodiments, the method includes operating the processor to: develop a convolutional neural network based on the set of training image patches.

In some embodiments, an architecture of the convolutional neural network includes three convolutional blocks, a global max pooling layer, a single fully-connected layer, and a sigmoid layer.

In some embodiments, the method includes operating the processor to define an architecture of the convolutional neural network by operating a Network Architecture Search (NAS).

In some embodiments, the method includes operating the processor to generate the feature extractor by applying one of pre-trained convolutional neural network, local binary patterns (LBP), Gabor filters, wavelet filters, and image differential filters.

In some embodiments, the method includes operating the processor to: generate a feature vector identifying the one or more tissue segments of the image patch.

In some embodiments, the method includes operating the processor to: generate a confidence score vector containing the confidence scores for each tissue type identified for the feature vector by the feature classifier.

In some embodiments, the confidence score vector has a size corresponding to a number of tissue types identified by the feature classifier for the image patch. The confidence score can include a continuous value.

In some embodiments, the method includes operating the processor to: map one or more prediction models to each tissue segment within the image patch to identify the tissue type relative to the training feature vector and class confidence score for that tissue type.

In some embodiments, the one or more prediction models includes a model based on at least one of a fully-connected (FC) network, a support vector machine (SVM), and a statistical regression.

In some embodiments, the feature classifier is based on a random-forest technique.

In some embodiments, the method includes operating the processor to: evaluate the confidence score generated by the feature classifier by comparing the confidence score with a confidence threshold; and generate a quality indicator indicating the confidence score satisfies the confidence threshold, and otherwise, generate the quality indicator indicating the confidence score fails to satisfy the confidence threshold.

In some embodiments, the quality indicator includes a Boolean value.

In some embodiments, the method includes operating the processor to construct the supervised digital pathology database by: receiving one or more image patches of normal tissue; receiving, via a labelling user interface, one or more user inputs to label each image patch with at least one tissue type according to the hierarchical histological taxonomy; storing each labelled image patch in the supervised digital pathology database.

In some embodiments, the method includes operating the processor to: select a subset of the training image patches stored in the supervised digital pathology database for verification; and receive, via a verification user interface, one or more user inputs to verify one or more labels associated with each training image patch of the subset the training image patches.

In some embodiments, the method includes operating the processor to: retrieve the set of training image patches from the supervised digital pathology database.

In some embodiments, the set of training image patches includes one or more image patches showing at least one normal tissue and the at least one normal tissue is labelled with a tissue type.

In some embodiments, the at least one normal tissue is labelled according to the hierarchical histological taxonomy.

In some embodiments, the method includes operating the processor to generate the one or more image patches from at least one whole slide image of a tissue specimen.

In some embodiments, the method includes operating the processor to: identify one or more regions of interest in the image patch from which to generate one or more image patches; and identify the one or more tissue types in each image patch of the one or more image patches.

In some embodiments, the one or more image patches includes at least one image patch having an overlapping portion with a neighbouring image patch.

In some embodiments, the method includes operating the processor to store the one or more image patches in an image patch database.

In some embodiments, the hierarchical histological taxonomy includes at least two hierarchical levels.

In some embodiments, the hierarchical histological taxonomy includes a set of morphological tissue type labels and a set of functional tissue type labels.

In accordance with an embodiment, there is provided a system for identifying an image patch associated with normal tissue. The system includes a processor operable to: apply a developed feature extractor to the image patch to identify one or more tissue segments within the image patch; apply a developed feature classifier to the one or more tissue segments to identify a respective tissue type and generate a corresponding confidence score representing a degree of similarity according to at least one prediction model generated based on a set of training image patches of a normal tissue of that tissue type, the tissue type being identified according to a hierarchical histology taxonomy; compare each confidence score generated by the feature classifier with a class confidence score generated for the normal tissue to determine whether the image patch is associated with normal tissue; and indicate a health state of each identified tissue type shown in the image patch based on the comparison of the confidence score with the class confidence score.

In some embodiments, the class confidence score includes a confidence score range and the processor is operable determine whether the confidence score falls within the confidence score range.

In some embodiments, the processor is operable to indicate the health state of the identified tissue type is normal when the confidence score satisfies the class confidence score associated to that tissue type, and abnormal when the confidence score fails to satisfy the class confidence score.

In some embodiments, the processor is operable to, in response to determining the health state of the identified tissue type is abnormal, mark the associated image patch to require further processing.

In some embodiments, the processor is operable to, in response to determining the health state of the identified tissue type is abnormal, generate a notification indicating that the associated image patch requires further processing.

In some embodiments, the system further includes a data storage operable to store the image patch identified by the processor to be associated with a normal health state. The data storage can include a normal image patch database for storing the image patch identified by the processor to be associated with the normal health state. The data storage can include an abnormal image patch database for storing the image patch identified by the processor to be associated with an abnormal health state.

In some embodiments, the system further includes a supervised digital pathology database having a set of training image patches stored thereon; and the processor is operable to: receive one or more image patches of normal tissue; receive, via a labelling user interface, one or more user inputs to label each image patch with at least one tissue type according to a hierarchical histological taxonomy; and store each labelled image patch in the supervised digital pathology database.

In some embodiments, the processor is in communication with the supervised digital pathology database and operable to: access the set of training image patches stored in the supervised digital pathology database; develop a feature extractor to generate a training feature vector identifying one or more training tissue segments in each training image patch in the set of training image patches; and develop a feature classifier to assign a tissue type to each training tissue segment identified in the training feature vector and to update a class confidence score for that tissue type, the tissue type being assigned according to the hierarchical histological taxonomy.

In some embodiments, the processor is in communication with the supervised digital pathology database and operable to: develop a convolutional neural network based on the set of training image patches.

In accordance with an embodiment, there is provided a method for identifying an image patch associated with normal tissue. The method includes operating a processor to: apply a developed feature extractor to the image patch to identify one or more tissue segments within the image patch; apply a developed feature classifier to the one or more tissue segments to identify a respective tissue type and generate a corresponding confidence score representing a degree of similarity according to at least one prediction model generated based on a set of training image patches of a normal tissue of that tissue type, the tissue type being identified according to a hierarchical histology taxonomy; compare each confidence score generated by the feature classifier with a class confidence score generated for the normal tissue to determine whether the image patch is associated with normal tissue; and indicate a health state of each identified tissue type shown in the image patch based on the comparison of the confidence score with the class confidence score.

In some embodiments, the class confidence score includes a confidence score range and the method includes operating the processor to determine whether the confidence score falls within the confidence score range.

In some embodiments, the method includes operating the processor to indicate the health state of the identified tissue type is normal when the confidence score satisfies the class confidence score associated to that tissue type, and abnormal when the confidence score fails to satisfy the class confidence score.

In some embodiments, the method includes operating the processor to, in response to determining the health state of the identified tissue type is abnormal, mark the associated image patch to require further processing.

In some embodiments, the method includes operating the processor to, in response to determining the health state of the identified tissue type is abnormal, generate a notification indicating that the associated image patch requires further processing.

In some embodiments, the method includes operating the processor to store the image patch identified to be associated with a normal health state in a data storage.

In some embodiments, the method includes operating the processor to: receive one or more image patches of normal tissue; receive, via a labelling user interface, one or more user inputs to label each image patch with at least one tissue type according to a hierarchical histological taxonomy; and store each labelled image patch in a supervised digital pathology database having a set of training image patches stored thereon.

In some embodiments, the method includes operating the processor to: access the set of training image patches stored in the supervised digital pathology database; develop a feature extractor to generate a training feature vector identifying one or more training tissue segments in each training image patch in the set of training image patches; and develop a feature classifier to assign a tissue type to each training tissue segment identified in the training feature vector and to update a class confidence score for that tissue type, the tissue type being assigned according to the hierarchical histological taxonomy.

In some embodiments, the method includes operating the processor to: develop a convolutional neural network based on the set of training image patches.

In accordance with an embodiment, there is provided a system for generating a pixel-level segmented image patch for an image patch. The system includes a processor operable to: apply a developed feature extractor to the image patch to identify one or more tissue segments within the image patch; apply a developed feature classifier to the one or more tissue segments to identify a respective tissue type and generate a corresponding confidence score representing a degree of similarity according to at least one prediction model generated based on a set of training image patches of a normal tissue of that tissue type, the tissue type being identified according to a hierarchical histology taxonomy; generate a class activation map for each identified tissue type based on the associated confidence score; and apply pixel-level segmentation to the class activation map to define a contour of each tissue segment of that tissue type to generate the pixel-level segmented image patch.

In some embodiments, the processor is operable to apply a gradient-class activation map (Grad-CAM) method to generate the class activation map.

In some embodiments, the processor is operable to: determine one or more tissue characteristics of the tissue type; and generate the class activation map based on the one or more tissue characteristics.

In some embodiments, the one or more tissue characteristics includes one of a morphological tissue type and a functional tissue type.

In some embodiments, the class activation map includes a pixel-level class activation map.

In some embodiments, the processor is operable to apply one or more post-processing techniques to the class activation map to increase a visual homogeneity of each tissue type segment.

In some embodiments, the one or more post-processing techniques includes a fully-connected conditional random field (CRF) modeling method.

In some embodiments, the processor is operable to adjust the class activation map with a background class activation map generated based on image data associated with high white-illumination values.

In some embodiments, the processor is operable to adjust the class activation map associated with a functional tissue type with a non-tissue class activation map generated based on image data associated with non-tissue characteristics.

In some embodiments, the system includes a supervised digital pathology database having a set of training image patches stored thereon; and the processor is operable to: receive one or more image patches of normal tissue; receive, via a labelling user interface, one or more user inputs to label each image patch with at least one tissue type according to a hierarchical histological taxonomy; and store each labelled image patch in the supervised digital pathology database.

In some embodiments, the processor is in communication with the supervised digital pathology database and operable to: access the set of training image patches stored in the supervised digital pathology database; develop a feature extractor to generate a training feature vector identifying one or more training tissue segments in each training image patch in the set of training image patches; and develop a feature classifier to assign a tissue type to each training tissue segment identified in the training feature vector and to update a class confidence score for that tissue type, the tissue type being assigned according to the hierarchical histological taxonomy.

In some embodiments, the processor is in communication with the supervised digital pathology database and operable to: develop a convolutional neural network based on the set of training image patches.

In accordance with an embodiment, there is provided a method for generating a pixel-level segmented image patch for an image patch. The method includes operating a processor to: apply a developed feature extractor to the image patch to identify one or more tissue segments within the image patch; apply a developed feature classifier to the one or more tissue segments to identify a respective tissue type and generate a corresponding confidence score representing a degree of similarity according to at least one prediction model generated based on a set of training image patches of a normal tissue of that tissue type, the tissue type being identified according to a hierarchical histology taxonomy; generate a class activation map for each identified tissue type based on the associated confidence score; and apply pixel-level segmentation to the class activation map to define a contour of each tissue segment of that tissue type to generate the pixel-level segmented image patch.

In some embodiments, the method includes operating the processor to apply a gradient-class activation map (Grad-CAM) method to generate the class activation map.

In some embodiments, the method includes operating the processor to: determine one or more tissue characteristics of the tissue type; and generate the class activation map based on the one or more tissue characteristics.

In some embodiments, the method includes operating the processor to apply one or more post-processing techniques to the class activation map to increase a visual homogeneity of each tissue type segment.

In some embodiments, the method includes operating the processor to adjust the class activation map with a background class activation map generated based on image data associated with high white-illumination values.

In some embodiments, the method includes operating the processor to adjust the class activation map associated with a functional tissue type with a non-tissue class activation map generated based on image data associated with non-tissue characteristics.

In some embodiments, the method includes operating the processor to: receive one or more image patches of normal tissue; receive, via a labelling user interface, one or more user inputs to label each image patch with at least one tissue type according to a hierarchical histological taxonomy; and store each labelled image patch in a supervised digital pathology database having a set of training image patches stored thereon.

In some embodiments, the method includes operating the processor to: access the set of training image patches stored in the supervised digital pathology database; develop a feature extractor to generate a training feature vector identifying one or more training tissue segments in each training image patch in the set of training image patches; and develop a feature classifier to assign a tissue type to each training tissue segment identified in the training feature vector and to update a class confidence score for that tissue type, the tissue type being assigned according to the hierarchical histological taxonomy.

In some embodiments, the method includes operating the processor to: develop a convolutional neural network based on the set of training image patches.

In accordance with an embodiment, there is provided a system for generating an encoded image patch for an image patch of at least one tissue. The system includes any system disclosed herein for generating a pixel-level segmented image patch of the image patch; and a processor operable to: generate one or more binary masks for the image patch, each binary mask being associated with an identified tissue type and corresponding to a pixel-level representation of one or more tissue segments of that tissue type; for each binary mask, identify one or more features related to a structure of each tissue segment; generate one or more feature correspondence values relating each feature identified in each binary mask and each tissue type identified for the image patch; and generate the encoded image patch based on the one or more feature correspondence values.

In some embodiments, the processor is operable to generate the feature correspondence value to represent a similarity of a structure of a tissue segment to a feature of the one or more features.

In some embodiments, the encoded image patch includes a matrix of the one or more feature correspondence values with a number of columns corresponding to a number of unique features identified in the one or more binary masks and a number of rows corresponding to a number of unique tissue types identified for the image patch.

In some embodiments, the processor is operable to generate a unique encoded image patch for each hierarchy level of the hierarchical histological taxonomy based on which the one or more tissue types are identified.

In some embodiments, the processor is operable to aggregate each unique encoded image patch to generate an aggregated encoded image patch.

In accordance with an embodiment, there is provided a method for generating an encoded image patch for an image patch of at least one tissue. The method includes operating a processor to: generate a pixel-level segmented image patch of the image patch according to any method disclosed herein; generate one or more binary masks for the image patch, each binary mask being associated with an identified tissue type and corresponding to a pixel-level representation of one or more tissue segments of that tissue type; for each binary mask, identify one or more features related to a structure of each tissue segment; generate one or more feature correspondence values relating each feature identified in each binary mask and each tissue type identified for the image patch; and generate the encoded image patch based on the one or more feature correspondence values.

In some embodiments, the method includes operating the processor to generate the feature correspondence value to represent a similarity of a structure of a tissue segment to a feature of the one or more features.

In some embodiments, the method includes operating the processor to generate a unique encoded image patch for each hierarchy level of the hierarchical histological taxonomy based on which the one or more tissue types are identified.

In some embodiments, the method includes operating the processor to aggregate each unique encoded image patch to generate an aggregated encoded image patch.

In accordance with an embodiment, there is provided a system for searching for one or more histological histopathological images. The system includes: a histopathological histological image databank constructed using any system disclosed herein; and a processor operable to: receive a search query defining one or more histopathological histological characteristics; and conduct a search of the histopathological histological databank for one or more encoded image patches that satisfies the search query.

In accordance with an embodiment, there is provided a method for searching for one or more histopathological images. The method includes operating a processor to: construct a histopathological image databank according to any method disclosed herein; receive a search query defining one or more histopathological characteristics; and conduct a search of the histopathological databank for one or more encoded image patches that satisfies the search query.

In accordance with an embodiment, there is provided a system for assigning an image patch to one or more pathological cases. The system includes: a histopathological histological image databank having a set of encoded image patches stored thereon and each encoded image patch is associated with a pathological case of the one or more pathological cases; and a processor in communication with the histopathological histological image databank and operable to: receive a whole slide image and divide at least a portion of the whole slide image into a plurality of image patches; determine using any system disclosed herein whether any image patch of the plurality of image patches is associated with abnormal tissue; in response to determining that an image patch of the plurality of image patches is associated with abnormal tissue, generate an encoded image patch of the image patch using any system disclosed herein; and compare the encoded image patch with the set of encoded image patches stored in the histopathological histological image databank to assign at least one pathological case to the encoded image patch.

In some embodiments, the processor is operable to construct the histopathological histological image databank by: receiving a set of training whole slide images, each training whole slide image associated with the one or more pathological cases; receiving, via a labelling user interface, user inputs associating at least one region within each training whole slide image with the one or more pathological cases; for each training whole slide image, generating a plurality of training image patches for the at least one region associated with the one or more pathological cases; generating an encoded training image patch using any system disclosed for each training image patch; and storing the encoded training image patch in the histopathological histological image databank in association with the associated one or more pathological cases.

In some embodiments, the processor is operable to store the encoded training image patch in one or more pathological case databases, each pathological case database being associated with a pathological case.

In accordance with an embodiment, there is provided a method for assigning an image patch to one or more pathological cases. The method includes operating a processor to: a histopathological image databank having a set of encoded image patches stored thereon and each encoded image patch is associated with a pathological case of the one or more pathological cases; and receive a whole slide image and divide at least a portion of the whole slide image into a plurality of image patches; determine whether any image patch of the plurality of image patches is associated with abnormal tissue according to any of the methods disclosed herein; in response to determining that an image patch of the plurality of image patches is associated with abnormal tissue, generate an encoded image patch of the image patch according to any method disclosed herein; and compare the encoded image patch with the set of encoded image patches stored in the histopathological image databank to assign at least one pathological case to the encoded image patch.

In some embodiments, the method includes operating the processor to: receive a set of training whole slide images, each training whole slide image associated with the one or more pathological cases; receive, via a labelling user interface, user inputs associating at least one region within each training whole slide image with the one or more pathological cases; for each training whole slide image, generate a plurality of training image patches for the at least one region associated with the one or more pathological cases; generate an encoded training image patch according to any method disclosed herein for each training image patch; and store the encoded training image patch in the histopathological image databank in association with the associated one or more pathological cases.

In some embodiments, the method includes operating the processor to store the encoded training image patch in one or more pathological case databases, each pathological case database being associated with a pathological case.

In some embodiments, the one or more pathological cases includes one or more disease types.

In accordance with some embodiments, there is provided a non-transitory computer-readable medium having instructions executable on a processor for implementing any one of the methods disclosed herein.

BRIEF DESCRIPTION OF THE DRAWINGS

Several embodiments will be described in detail with reference to the drawings, in which:

FIG. 4 is a table illustrating an example hierarchical histological taxonomy, in accordance with an example embodiment;

FIG. 5 is a subset of the table shown in FIG. 4 embedded with example histological images;

Figure 1:
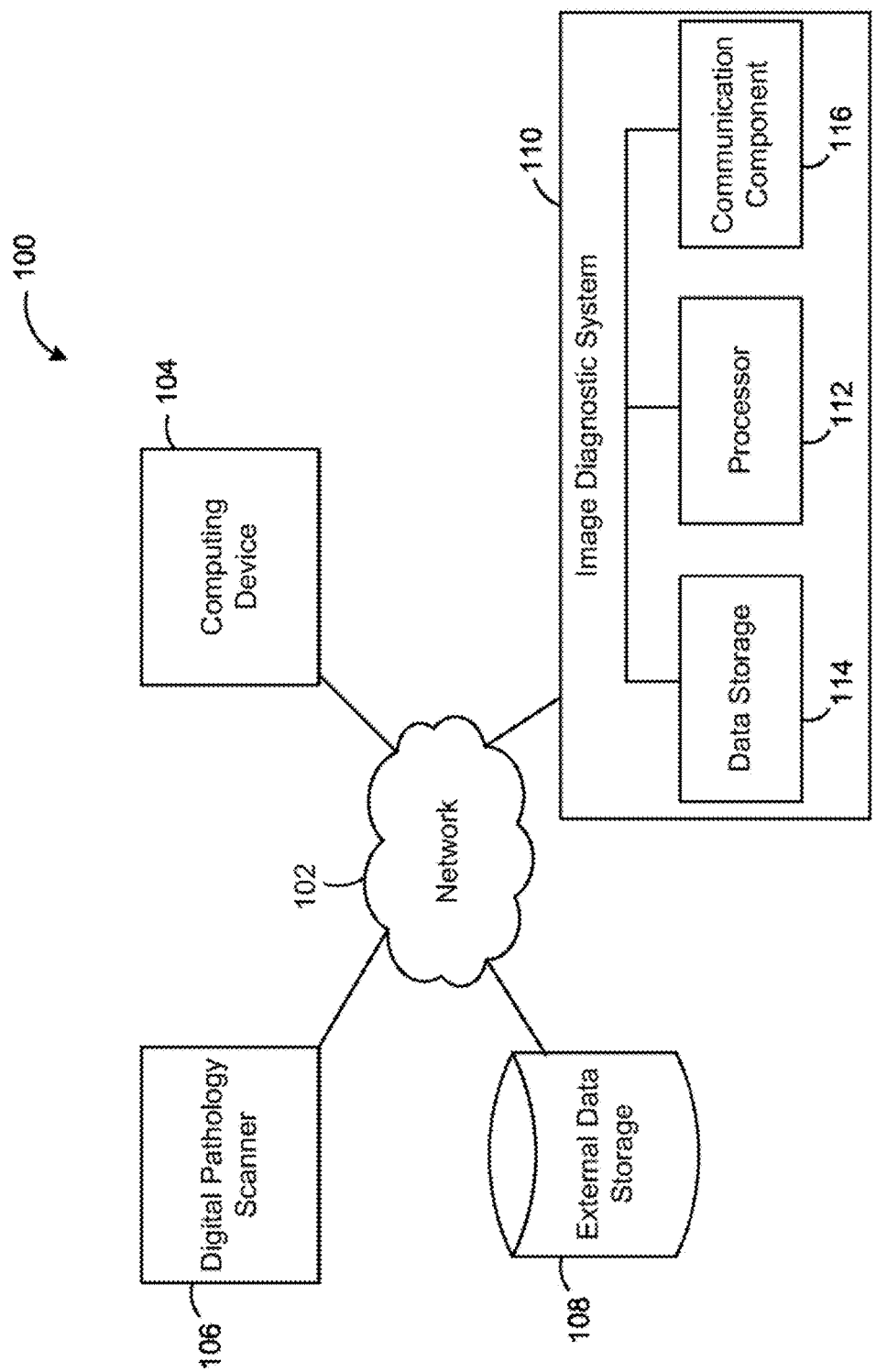
FIG. 1 is a block diagram of an example image diagnostic system in communication with example external components, in accordance with an example embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

To diagnose a tissue specimen, a glass slide is prepared with the tissue specimen for microscopy scanning. The glass slide can then be converted into a digital slide by a digital pathology scanner, such as a whole slide imaging device. The digital slide is then examined to identify relevant regions, or regions of interest (ROIs), which are then diagnosed for disease. Screening for regions of interests can be a tedious and time-consuming visual recognition task as imaged pathological slides are very large in size (for example, many can have a size greater than 100 MB). For example, a pathologist diagnosing a tissue specimen for adenocarcinoma will first screen for glandular tissue regions, and review those regions that appear abnormally disordered before assigning a diagnosis. In addition, pathologists are often required to diagnose hundreds to thousands of slides each day. As a result, diagnostic accuracy can suffer when the pathologists are fatigued.

The tissue specimen can relate to any biological systems, such as animal and plants.

Automating the screening process to separate normal tissue and diseased tissue can, therefore, increase the efficiency and reduce the turnaround time for diagnosing the tissue specimens. Normal tissues refer to tissues that are diagnosed to be healthy and unaffected by a known disease. Existing screening tools are typically limited to a specific task and cannot be extended to other tasks, such as the identification of other types of diseases or other grades of cancer, since the appearance and structure of abnormalities in diseased tissues can be highly variable. For example, a tool can be limited to identifying only metastatic breast cancer from sentinel lymph node biopsies. Also, existing tools typically require considerable quantities of abnormal tissue samples in order to generate a training data set.

Existing diagnostic computational tools require pixel-level annotation of histological tissue type (HTT) when segmenting whole slide images. However, pixel-level annotation is impractical due to the significant time and effort required by pathologists. In the methods and systems described herein, glass slides are digitized and then divided into image patches, or sub-images. An image patch corresponds to a portion of an image. The size of the image portion can vary and will typically relate to a small portion of the image. The number of image patches divided from an image can vary according to the size of the image, characteristics of the image, and/or features shown in the image. In some embodiments, the dimensions of an image patch can be selected based on the resolution necessary to show sufficient tissue information to facilitate the analysis of that tissue.

The disclosed systems can then develop a feature extractor and classifier for the image patches by training a neural network on a digital pathology database. The training datasets relate to normal tissues. By operating to identify normal tissues based on their appearance and/or structure, the disclosed systems can be extended to apply to any disease type as there is no requirement for data related to the abnormal tissue samples to serve as training datasets.

The image patches can then be labelled by the feature extractor and classifier according to a hierarchical histological taxonomy. Training a neural network on image patches labelled based on labels established according to the hierarchical histological taxonomy can, in some embodiments, capture more relevant information. Certain visual features which enable the distinction between more specific tissue types may not be shown, or not clearly shown, in some images while those visual features are visible in other images. To enable clear and informative labelling, a higher-level label is helpful for the images that do not show (or do not dearly show) those visual features and more specific labels are available for images that show those features.

Based on the patch-level annotations, the disclosed systems and methods can predict tissue types at the pixel level.

The methods and systems described herein can reduce the cognitive workload required of pathologists by narrowing the visual search area by highlighting (or segmenting) regions of diagnostic relevance. Pathologists are able to then focus on diagnosing the relevant regions of interest. The applications of the methods and systems disclosed herein can be extended to, but not limited to, toxicological analysis, forensic sciences, and other related fields.

Reference is first made to FIG. 1, which illustrates an example block diagram 100 of an image diagnostic system 110 in communication with a digital pathology scanner 106, an external data storage 108, and a computing device 104 via a network 102. Although only one digital pathology scanner 106 and one computing device 104 are shown in FIG. 1, the image diagnostic system 110 can be in communication with a greater number of digital pathology scanners 106 and/or computing devices 104. The image diagnostic system 110 can communicate with the digital pathology scanner(s) 106 and computing device(s) 104 over a wide geographic area via the network 102.

The digital pathology scanner 106 can include any computing device that is capable of capturing image data, generating image data, and/or storing image data. The digital pathology scanner 106 can scan glass slides held by racks, for example.

The digital pathology scanner 106 can include a computing device 104, in some embodiments. For example, the digital pathology scanner 106 can include a whole slide imaging scanner that digitizes glass slides. Whole slide imaging scanners are often used in digital pathology to digitize glass slides by scanning through the regions of interest with high magnification optics. Depending on the intended purpose of the digital glass slides, the whole slide imaging scanner can be operated using different magnification optics. The digital images obtained from whole slide imaging scanners are stored at high resolution. The digital images can be accessed by users, via a computer display, to interact (e.g., visualize, navigate, focus, mark, and classify, etc.) with the regions of interest within the digital slide.

The image diagnostic system 110 includes a processor 112, a data storage 114, and a communication component 116. The image diagnostic system 110 can be implemented with more than one computer server distributed over a wide geographic area and connected via the network 102. The processor 112, the data storage 114 and the communication component 116 may be combined into a fewer number of components or may be separated into further components.

The processor 112 can be implemented with any suitable processor, controller, digital signal processor, graphics processing unit, application specific integrated circuits (ASICs), and/or field programmable gate arrays (FPGAs) that can provide sufficient processing power for the configuration, purposes and requirements of the image diagnostic system 110. The processor 112 can include more than one processor with each processor being configured to perform different dedicated tasks.

The communication component 116 can include any interface that enables the image diagnostic system 110 to communicate with various devices and other systems. For example, the communication component 116 can receive an image generated by the digital pathology scanner and store the image in the data storage 114 or external data storage 108. The processor 112 can then process the image according to the methods described herein. In some embodiments, the image diagnostic system 110 can receive data directly from the digital pathology scanner 106. For example, the image diagnostic system 110 can receive images directly from the digital pathology scanner 106 as the image is being generated. This can further reduce delays in analyzing the images.

The communication component 116 can include at least one of a serial port, a parallel port or a USB port, in some embodiments. The communication component 116 may also include an interface to component via one or more of an Internet, Local Area Network (LAN), Ethernet, Firewire, modem, fiber, or digital subscriber line connection. Various combinations of these elements may be incorporated within the communication component 116. For example, the communication component 116 may receive input from various input devices, such as a mouse, a keyboard, a touch screen, a thumbwheel, a track-pad, a track-ball, a card-reader, voice recognition software and the like depending on the requirements and implementation of the image diagnostic system 110.

The data storage 114 can include RAM, ROM, one or more hard drives, one or more flash drives or some other suitable data storage elements such as disk drives. The data storage 114 can include one or more databases for storing data related to the hierarchical representation of tissue types, and/or image data related to normal tissues and/or non-disease artifacts.

In some embodiments, the data storage 114 can be used to store an operating system and programs. For instance, the operating system provides various basic operational processes for the processor 112. The programs include various user programs so that a user can interact with the processor 112 to perform various functions such as, but not limited to, viewing and/or manipulating the images as well as retrieving and/or transmitting image data.

The data storage 114 can store images, including versions of the images at different resolutions, information about the glass slide from which the image was generated, classification information related to the images, information related to reports associated with the images, for example, diagnoses with respect to the image data, images of normal tissues, and images of tissues containing non-disease artifacts. Non-disease artifacts can be introduced during the preparation of the slide and can include, but is not limited to, cross-contamination, air bubbles, dust specks, folded tissue, crushed tissue, torn tissue, cut tissue, cracked tissue, tissue fixation, tissue thickness, and other defects.

The data storage 114 can store information related to image labels, such as but not limited to, text comments, audio recordings, markers, shapes, lines, free form mark-ups, and measurements.

The external data storage 108 can store data similar to that of the data storage 114. The external data storage 108 can, in some embodiments, be used to store data that is less frequently used and/or older data. In some embodiments, the external data storage 108 can be a third party data storage stored with image data for analysis by the image diagnostic system 110. The data stored in the external data storage 108 can be retrieved by the computing device 104 and/or the image diagnostic system 110 via the network 102.

Images described herein can include any digital image of any reasonable size and resolution for histological and pathological applications. In some embodiments, the image diagnostic system 110 can apply image pre-processing to the images, such as but not limited to normalizing the pixel dimensions of an image and/or digital filtering for noise reduction, and storing the pre-processed image as a version of the original image. Example images can include a histological image of a tissue, or part of a tissue, and a histopathological image of a tissue, or a part of a tissue. Histological images relate to normal tissues, whereas histopathological images relate to abnormal and normal tissue within the same tissue section. The images can be generated using a microscope. Each image can have an intensity value associated with each pixel.

The computing device 104 can include any device capable of communicating with other devices through a network such as the network 102. A network device can couple to the network 102 through a wired or wireless connection. The computing device 104 can include a processor and memory, and may be an electronic tablet device, a personal computer, workstation, server, portable computer, mobile device, personal digital assistant, laptop, smart phone, WAP phone, an interactive television, video display terminals, gaming consoles, and portable electronic devices or any combination of these.

The network 102 can include any network capable of carrying data, including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these, capable of interfacing with, and enabling communication between, the image diagnostic system 110, the digital pathology scanner 106, the external data storage 108, and the computing device 104.

Figure 2A:
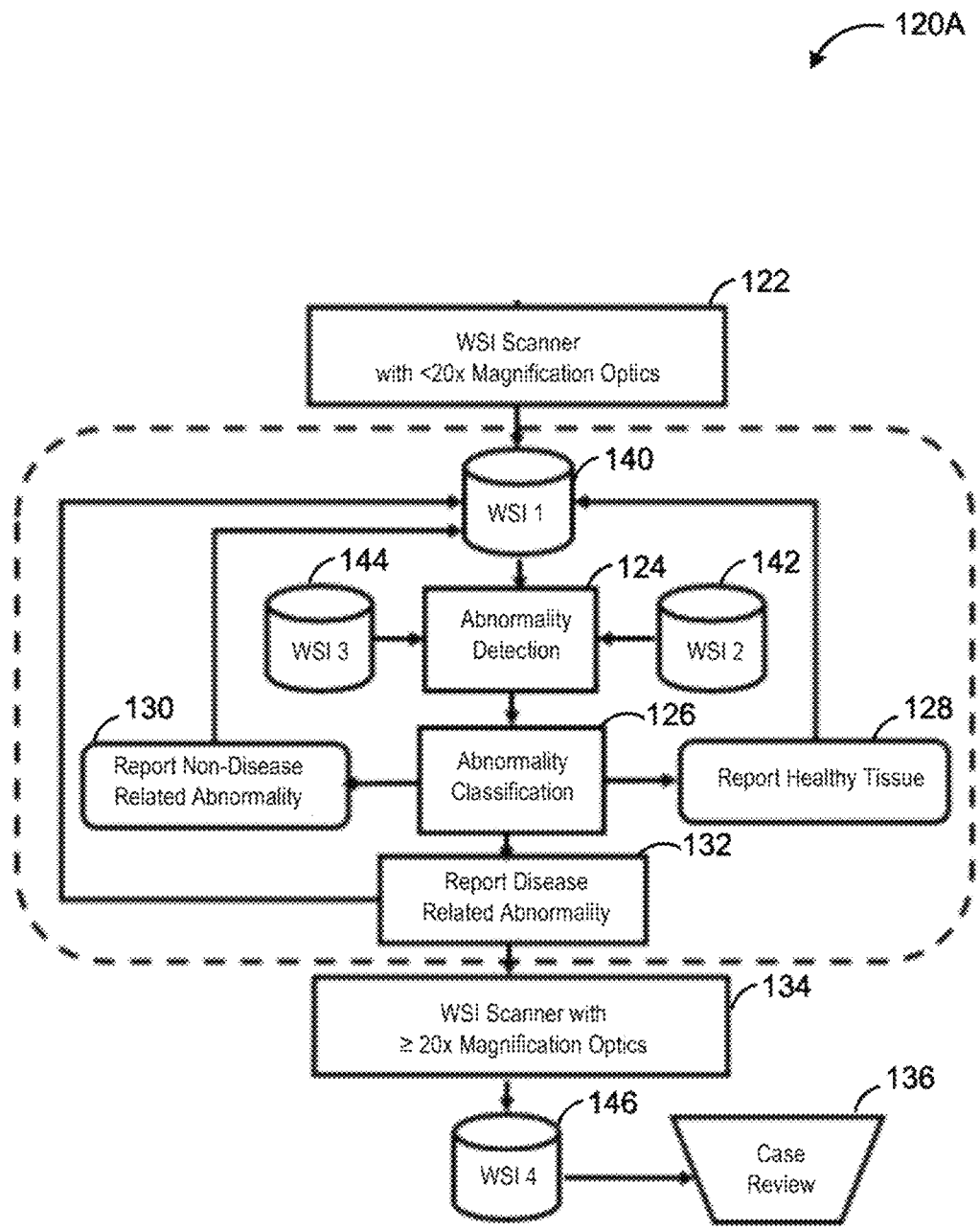
FIG. 2A is a flowchart of an example method for operating the image diagnostic system for screening one or more slides, in accordance with an example embodiment.

Reference will now be made to FIG. 2A, which shows a flowchart 120A illustrating an example method of operating the image diagnostic system 110 for screening one or more glass slides.

At 122, the image diagnostic system 110 operates to obtain a digital image of each glass slide. Glass slides can be stored on a slide rack. The image diagnostic system 110 can operate the digital pathology scanner 106 (such as a whole slide imaging device), to generate the digital images of the glass slides.

The digital pathology scanner 106 can be operated to generate the digital slides at low-resolution, such as at a magnification of 20 times (20X) or less. The image diagnostic system 110 can store the low-resolution digital image obtained at 122 into a low-resolution database, such as database 140 ("WSI 1"). The database 140 can be provided with data storage 114, 108, for example.

At 124, the image diagnostic system 110 then applies the methods disclosed herein to determine whether the digital image generated at 122 is associated with normal tissue or non-disease artifacts. As will be described, the methods applied by the image diagnostic system 110 can refer to images stored in databases 142 ("WSI 2") and 144 ("WSI 3"). For example, database 142 can store images related to normal tissues and database 144 can store images related to non-disease artifacts. The databases 142, 144 can be provided with data storage 114, 108, for example.

At 126, the image diagnostic system 110 can classify each digital image accordingly. For digital images classified as relating to normal tissue, the image diagnostic system 110 can classify the digital image as normal (at 128) and store the relevant information at database 140 in association with the digital image. Similarly, for digital images classified as relating to non-disease artifacts, the image diagnostic system 110 can classify the digital image as non-disease artifact (at 130) and store the relevant information at database 140 in association with the digital image.

At 132, the image diagnostic system 110 can classify the remaining digital images to relate to abnormal tissue (at 132). In some embodiments, the image diagnostic system 110 can also conduct the methods disclosed herein to identify one or more pathological case with the abnormal tissue within the digital image.

At 134, the image diagnostic system 110 can operate the digital pathology scanner 106 to generate a high-resolution digital image of the glass slides corresponding to the digital images associated with abnormal tissue. The high-resolution digital image can be at a magnification of 20 times or greater, for example. The image diagnostic system 110 can use a different digital pathology scanner 106 than at 122, in some embodiments.

The image diagnostic system 110 can then store the high-resolution digital images in a database 146 ("WSI 4"). The database 146 can be provided with data storage 114, 108, for example.

In some embodiments, databases 140, 142, 144, 146 can be provided together in one or more data storages or separately in different data storages. One or more of databases 140, 142, 144, 146 can be provided together, while the others provided separately.

At 136, the image diagnostic system 110 can indicate that the high-resolution digital images are available for review by a pathologist, for example. In some embodiments, the image diagnostic system 110 can generate a notification indicating the high-resolution digital images are ready for review.

Figure 2B:
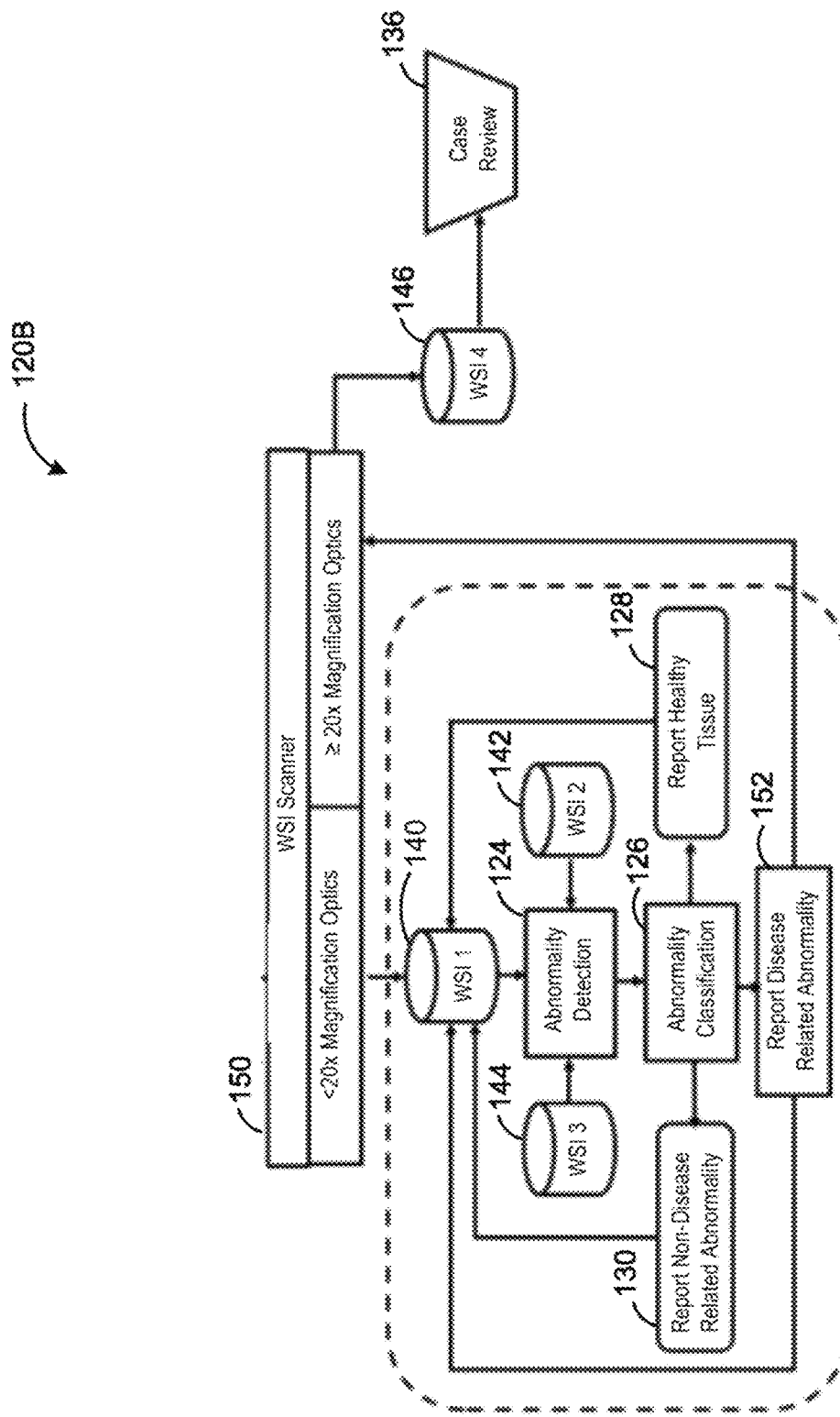
FIG. 2B is a flowchart of another example method for operating the image diagnostic system for screening one or more slides, in accordance with an example embodiment.

Reference is now made to FIG. 2B, which is a flowchart 120B illustrating another example method of operating the image diagnostic system 110 for screening one or more glass slide. The method shown in FIG. 2B is generally similar to that shown in FIG. 2A, except that, at 150 and 152, when the image diagnostic system 110 operates to obtain digital images at low-resolution and high-resolution, the image diagnostic system 110 can operate the same digital pathology scanner 106.

As will be described, the image diagnostic system 110 can be operated to develop a neural network on a digital pathology database. The image diagnostic system 110 can receive image patches of normal tissues that are labelled according to an established histological taxonomy and store the labelled image patches into the digital pathology database as the training dataset. The digital pathology database can store labelled images and/or labelled image patches related to normal tissues, abnormal tissues and/or artifacts. This digital pathology database can be referred to as the supervised digital pathology database and can be provided in the data storage 114 and/or external data storage 108. In some embodiments, as shown generally in FIG. 3, the image diagnostic system 110 can operate to receive whole slide images of normal tissues (at 210), divide the digitized slides of the whole slide images into image patches (at 220) and provide a user interface from which to receive user inputs labelling each image patch according to the established histological taxonomy (at 230).

The histological taxonomy can follow any histological classification system as long as the classification system is consistently applied throughout the digital pathology database. Generally, histological taxonomy can be developed by referring to existing histology documents that are used as educational materials for students in histology, knowledge of pathologists (e.g., via consultation with expert pathologists), and example tissue specimens. However, to extend the application of the image diagnostic system 110 beyond specific disease types, the labels and image data available via the digital pathology database is important. For example, some digital pathology databases include images that are labelled at the glass slide level and therefore, include minimal localized information. Digital pathology slide images are typically very large and by labeling at the glass slide level, the labels can be incomplete and exclude essential regions of interest. Some digital pathology databases include histopathological images that are specially labelled for certain diseases. As a result, the image diagnostic system 110 cannot use those labelled histopathological images to develop the neural network to be generalized to classify unexpected diseases or unseen organs.

The operation of the image diagnostic system 110 can benefit from a digital pathology database with image patches that are labelled according to a histological taxonomy system that involves a large range of tissue types. As will be described with reference to FIGS. 4 and 5, with the current microscopic technologies, there are only a limited number of tissue types that are observable. Further tissue types may be observable with evolving microscopic technologies. The scope of the image diagnostic system 110 is not limited to the existing observable tissue types. The example hierarchical histological taxonomy 280 illustrated in FIGS. 4 and 5 can be adapted with additional knowledge from pathologists and data resulting from the use of new technologies. By operating the image diagnostic system 110 to develop the neural network on image patches labelled with a large range of tissue types, the image diagnostic system 110 can generate valuable results to pathologists that, in some embodiments, can be beyond the capabilities of pathologists achievable via the manual screening process.

Also, as described herein, operating the image diagnostic system 110 to develop the neural network on image patches labelled according to a hierarchical histological taxonomy can capture more relevant information. Certain visual features which enable the distinction between more specific tissue types may not be shown, or not clearly shown, in some images while those visual features are visible in other images. To enable clear and informative labelling, a higher-level label is helpful for the images that do not show (or do not clearly show) those visual features and more specific labels are available for images that show those features.

FIG. 4 illustrates at 280 an example hierarchical histological taxonomy table, and FIG. 5 illustrates a portion 300 of the hierarchical histological taxonomy table 280 embedded with example histological images for illustrative purposes.

In general, tissue types can be characterized with specific visual patterns and relative spatial relationships. For example, epithelial tissues can be characterized by linearly-arranged nuclei-dense cells lining a surface, connective proper tissues can be characterized by long fibrous cells with scant nuclei between other tissues, blood tissues can be characterized by circular or ovoid blobs which sometimes dump together and are often inside transport vessels, and skeletal tissues can be characterized by a woody material which sometimes contains layered rings and sometimes appears mottled with lighter regions, adipose tissues can be characterized by clustered rings or bubbles, muscular tissues can be characterized by parallel (e.g., longitudinal cut) or bundled (e.g., transverse cut) dense fibrous cells with oblong nuclei, nervous tissues can be characterized by wispy strands connecting branching circular blobs, glandular tissues can be characterized by epithelium-lined ovoid structures with or without inner openings, and transport vessel tissues can be characterized by string-like rings often containing blood.

In the example hierarchical histological taxonomy 280, the tissue types are assigned into different types of varying specificity based on aspects related to their morphology and functionality, and how they relate to each other. Morphology relates to a tissue structure, whereas functionality refers to tissue functionality and relation to organs. Classification of tissues based on morphology is often used because even a small visual field is sufficient to identify the tissue structure, whereas classification by functionality is not as often used when labelling image patches since the organ of origin of the tissue specimen is usually unknown and a larger visual field is needed to provide the spatial context for understanding the tissue functionality.

In the example hierarchical histological taxonomy 280, tissue types of differing specificity are organized vertically in a parent-child relationship. Tissue types with the same parent node and specificity are organized in a sibling relationship. For example, simple epithelial and stratified epithelial tissues are respective child nodes of the parent node, epithelial tissue. The hierarchical histological taxonomy 280 continues to classify the tissue types until leaf nodes are reached.

In some embodiments, the hierarchical histological taxonomy 280 can be encoded with a hierarchical encoding system so that each node is associated with a nodal code. For example, a nodal code can be generated based on a concatenation of its ancestor nodes' symbols (e.g. the stratified cuboidal epithelial node is encoded as "E.T.U.", as its ancestors are symbolized by "E.T." (stratified epithelial) and "E" (epithelial). When a label for an image patch cannot be assigned with a leaf node, a placeholder code can applied. For example, when a stratified epithelial tissue cannot be assigned a nodal code corresponding to a leaf node, the stratified epithelial undifferentiated leaf node, represented by the nodal code "E.T.X", can be used. Other manners of labelling undifferentiated tissue types can be applied.

The example hierarchical histological taxonomy 280 is organized into three hierarchical levels, a first hierarchical level 290, a second hierarchical level 292 and a third hierarchical level 294. The first hierarchical level 290 includes nine parent nodes corresponding to epithelial tissues, connective proper tissues, blood tissues, skeletal tissues, adipose tissues, muscular tissues, nervous tissues, glandular tissues, and transport vessel tissues.

The second hierarchical level 292 builds from the first hierarchical level 290. For example, epithelial tissue is a parent node within the first hierarchical level 290 and is associated with child nodes associated with simple epithelial tissue and stratified epithelial tissue, and pseudostratified epithelial tissue in the second hierarchical level 292.

The third hierarchical level 294 builds from the second hierarchical level 292. For example, simple epithelial tissue is a child node within the second hierarchical level 292 and is associated with grandchild nodes associated with simple squamous epithelial tissue, simple cuboidal epithelial tissue, and simple columnar epithelial tissue in the third hierarchical level 294.

As shown in FIGS. 4 and 5, it is impossible for a child node in the second hierarchical level 292 to be a leaf node (e.g., pseudostratified epithelial tissue). It is also possible for a parent node to be a leaf node (e.g., transport vessel tissue).

Figure 3:
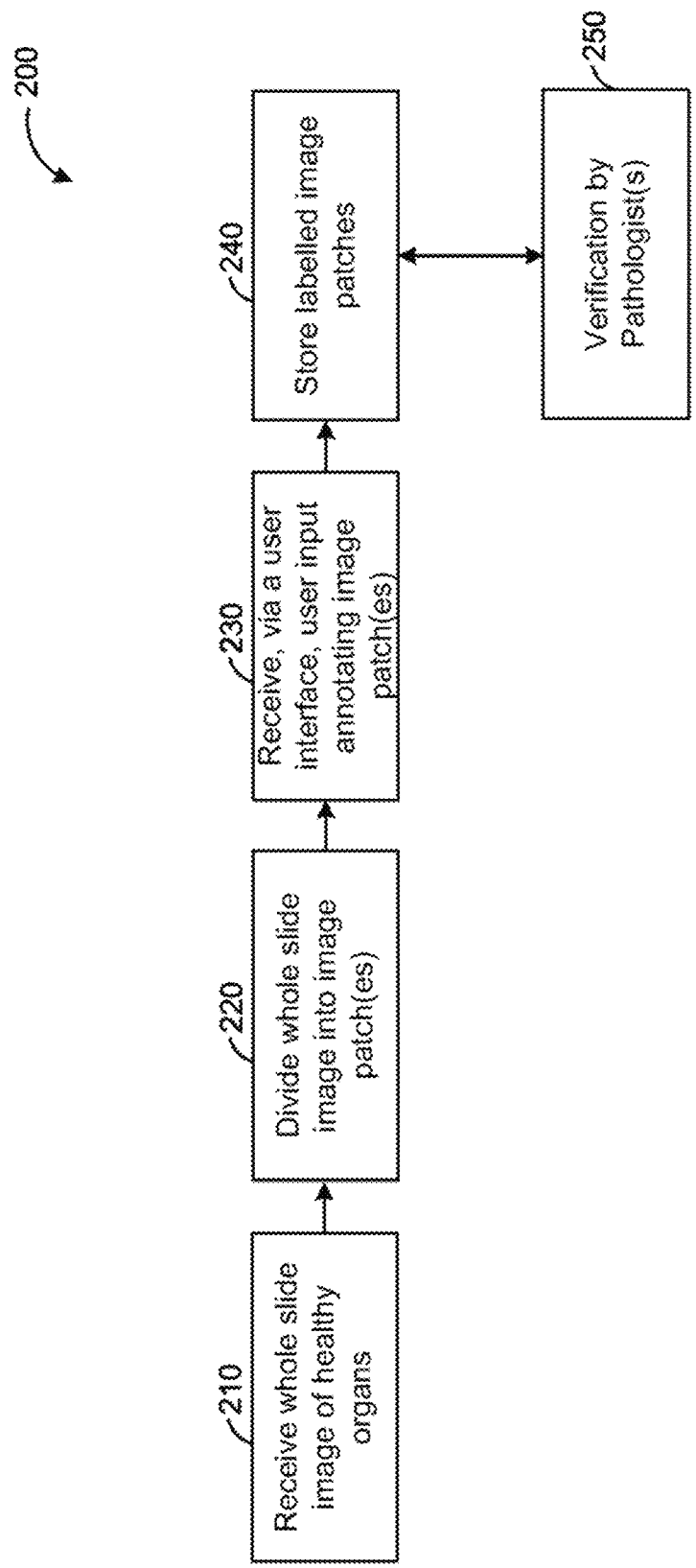
FIG. 3 is a flowchart of an example method for constructing a digital pathology database, in accordance with an example embodiment.

Continuing with reference to FIG. 3, at 230, the image diagnostic system 110 can receive, via a user interface, the user inputs labelling each image patch according to the example hierarchical histological taxonomy 280. The user inputs can be received from one or more histology labeling experts who are trained to recognize tissues according to the hierarchical histological taxonomy 280. The user interface can also receive multiple labels for each image patch and different labels from each user. Digital pathology slides contain visibly recognizable tissues and so, the image diagnostic system 110 can receive user inputs related to one or more histological tissue types.

After the image diagnostic system 110 receives the user inputs, the image diagnostic system 110 can store (240) the labelled image patches in the supervised digital pathology database in the data storage 114 and/or 108. As quality control, the labelled image patches can be reviewed by experienced pathologists at 250. The experienced pathologists can be board-certified and are usually very expensive. For the purpose of quality control, the image diagnostic system 110 can select a subset of labelled image patches for the experienced pathologists to verify.

With reference to the supervised digital pathology database in the data storage 114 and/or 108, the image diagnostic system 110 can proceed with analyzing new whole slide images. As will be described with reference to FIGS. 6 to 18, the image diagnostic system 110 can, at least, identify tissue types within image patches and also outline individual tissue segments for tissue type quantification (e.g. measuring lymphocyte density or epithelium thickness); identify abnormal tissue regions (e.g. cancerous tumors, slide imperfections, staining debris, and out-of-focality) from class confidence scores generated by the neural network when identifying the tissue types; and encoding tissue types to facilitate feature searching within the supervised digital pathology database 114, 108 (e.g. text-based image retrieval).

Figure 6:
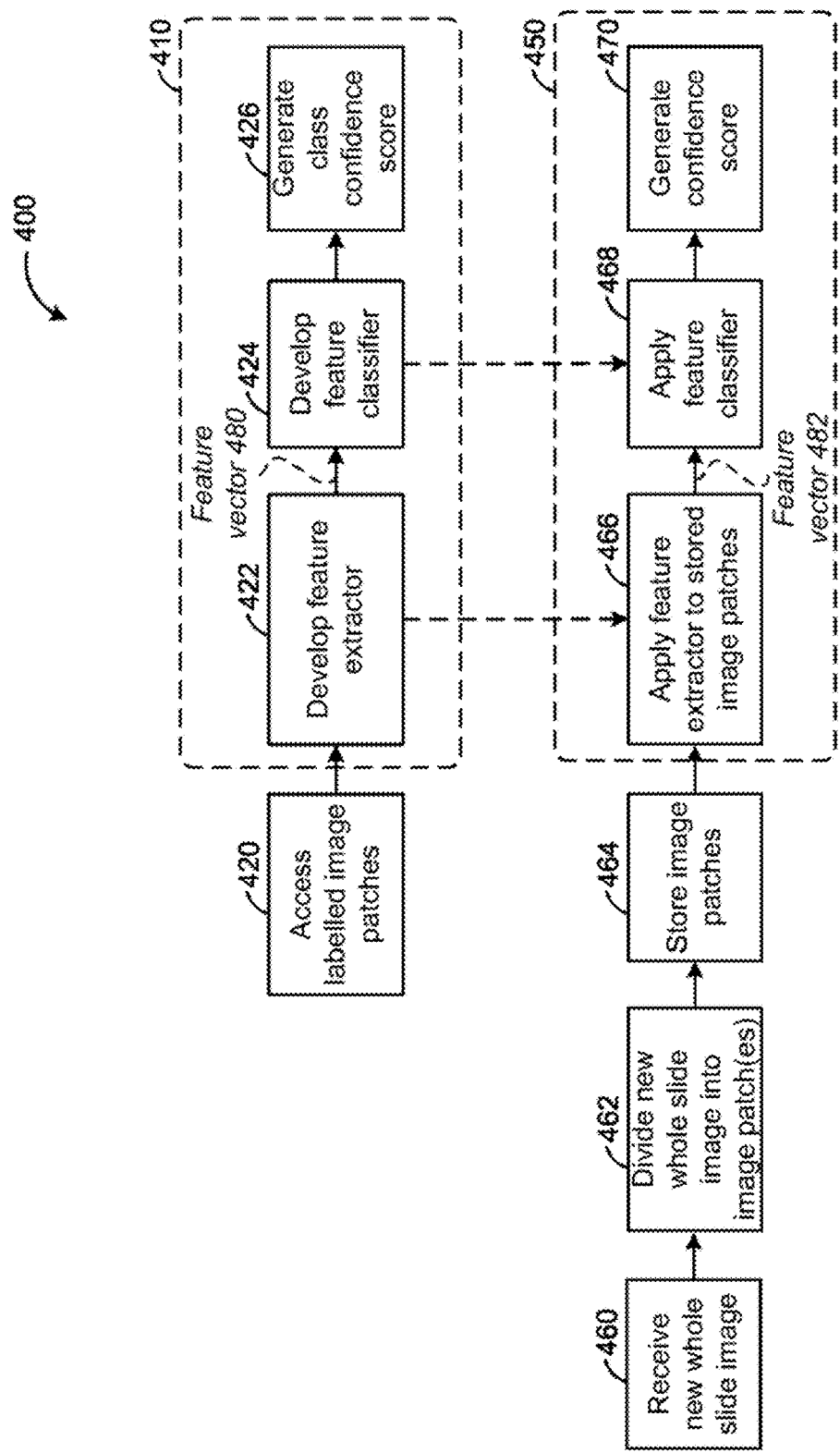
FIG. 6 is a flowchart of an example method of operating the image diagnostic system to automatically identify tissue types within an image patch of a whole slide image, in accordance with an example embodiment.
Figure 7A:
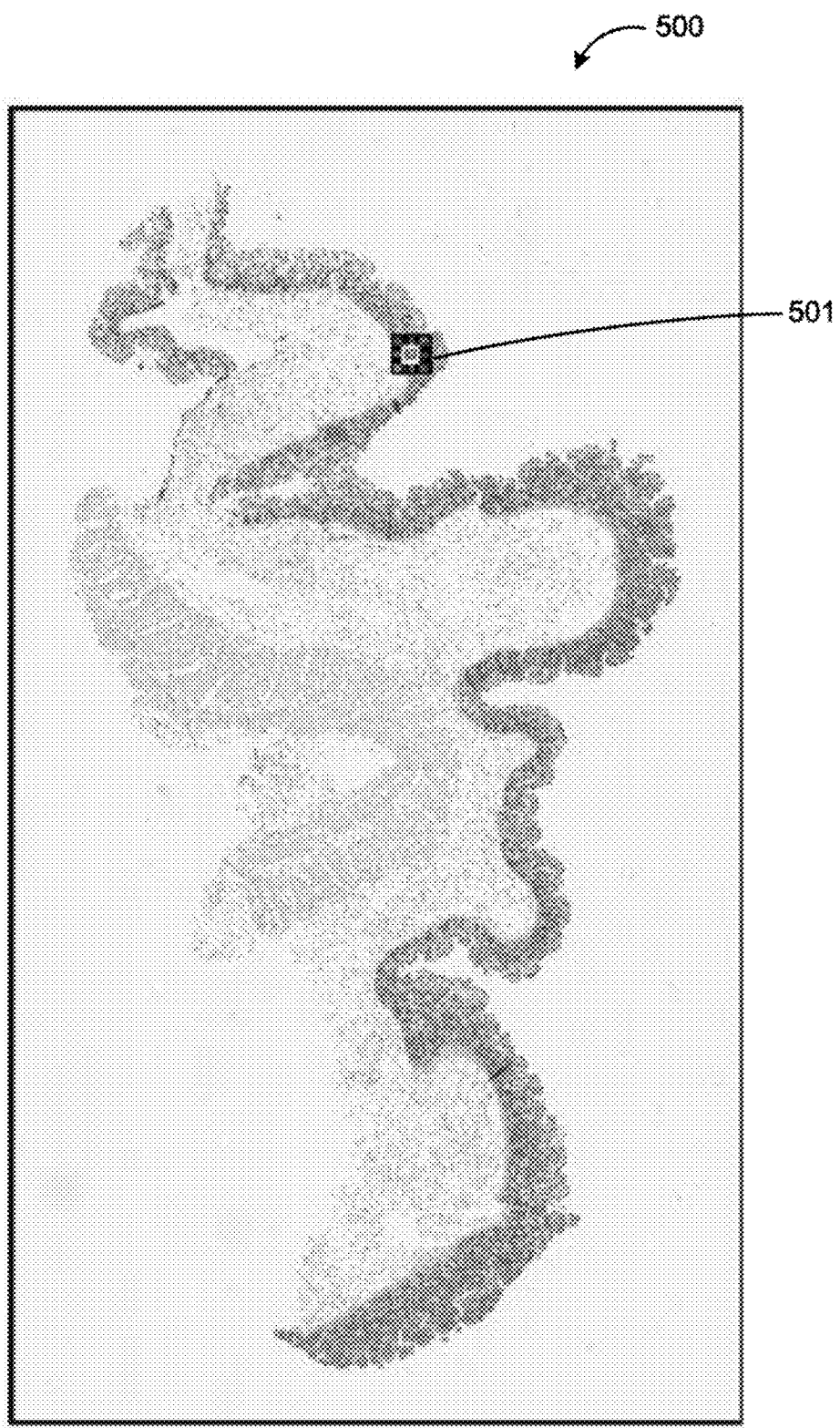
FIG. 7A shows an example whole slide image.
Figure 7C:
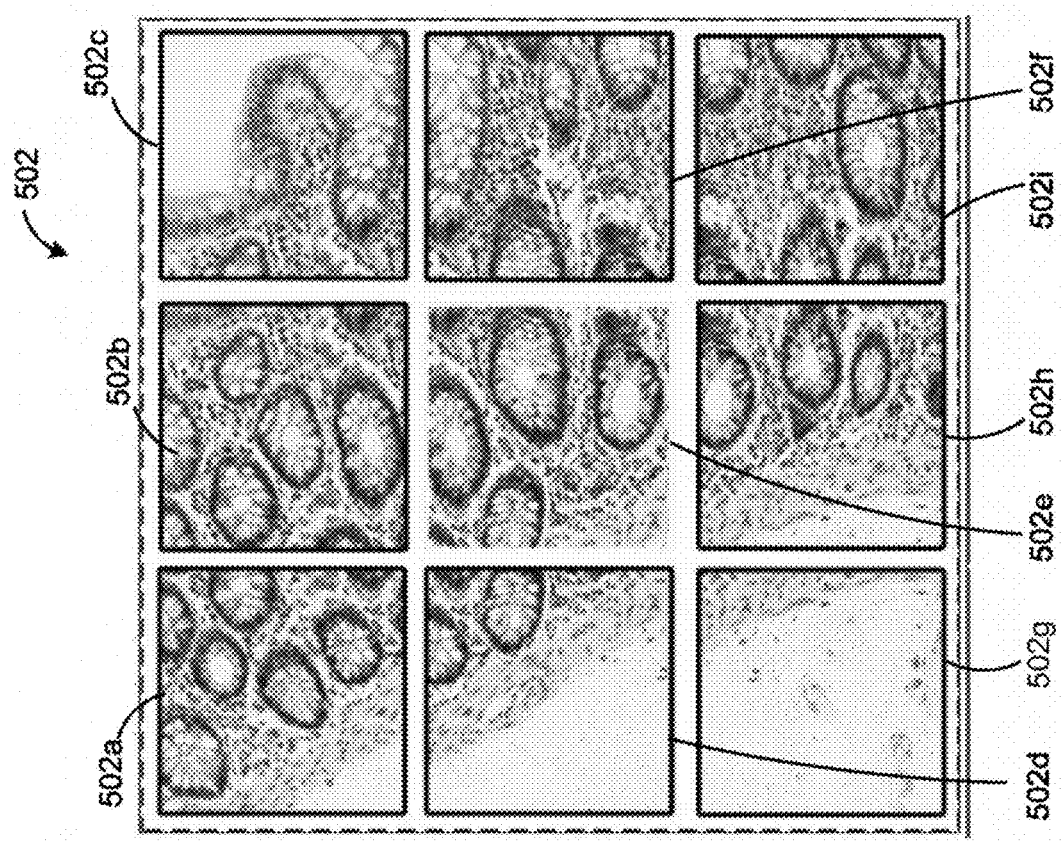
FIG. 7C shows the example image patches generated from the portion of the whole slide image of FIG. 7B.
Figure 7B:
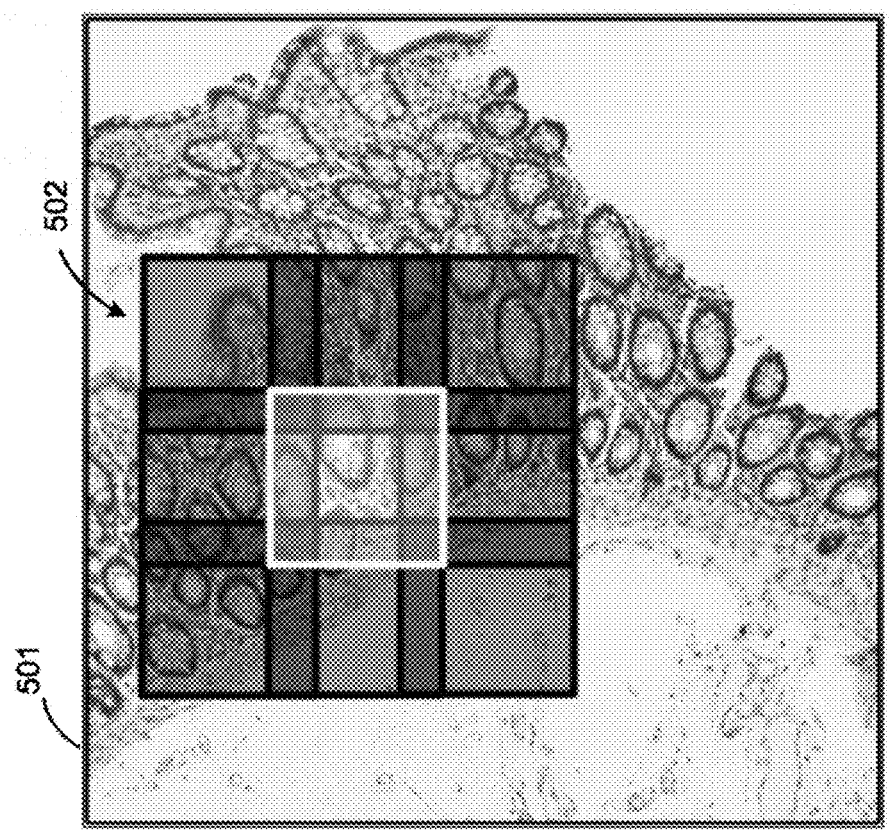
FIG. 7B shows a portion of the whole slide image of FIG. 7A with an example set of image patches.

Reference will now be made to FIG. 6, which shows a flowchart 400 of an example method of operating the image diagnostic system 110 to automatically identify one or more tissue types within an image patch of a whole slide image. FIG. 7A shows an example whole slide image 500, FIG. 7B shows an example region of interest 501 of the whole slide image 500, and FIG. 7C shows example image patches 502 selected from the region of interest 501 of the whole slide image 500. As shown in FIGS. 7B and 7C, the region of interest 501 can include multiple overlapping image patches 502.

In FIG. 6, an example training and validation phase is shown at 410 and an example classification phase is shown at 450.

During the training and validation phase 410, the image diagnostic system 110 accesses (420) the labelled image patches from the supervised digital pathology database 114, 108. The image diagnostic system 110 can retrieve the labelled image patches for the training and validation phase 410, in some embodiments. The labelled image patches in the supervised digital pathology database 114, 108 can be labelled according to the hierarchical histological taxonomy table 280 of FIG. 4. The labelled image patches stored in the supervised digital pathology database 114, 108 can serve as the training image patches during the training and validation phase 410. The image diagnostic system 110 can develop a feature extractor with the training image patches and update the parameters of the feature extractor according to the hierarchical labels assigned to the training image patches.

At 422, the image diagnostic system 110 operates to develop the feature extractor using the training image patches. The feature extractor will then be applied by the image diagnostic system 110 to other image patches to identify the tissue types shown therein.

The feature extractor can be trainable or non-trainable. A trainable feature extractor can be developed based on data-driven methods, such as the layers of a convolutional neural network (CNN) before the fully-connected layers (e.g., the convolution and pooling layers). A non-trainable feature extractor can include handcrafted methods, such as, but not limited to, local binary patterns (LBP), pre-trained convolutional neural network via transferable learning, wavelet filters, image differential filters and Gabor filters.

Convolutional neural networks generally include convolutional and pooling layers to downsample the training dataset, followed by fully connected layers that generate the desired predictions. The convolution operations involve element-wise matrix multiplication between filter values and the pixels in the image, and the resultant values are then summed. During the pooling layer, information collected by the convolution layer is simplified and condensed. The pooling operation can involve reducing the network parameters (e.g., size of a filter window, number of filters, a stride and padding), which can then reduce the required computation. Convolutional neural networks are deep, feed forward neural networks as they are trained through iterative passes at the training dataset. With each iteration, a further layer of the convolutional neural network is able to identify more complex features. Different architectures of the convolutional neural networks can be applied herein, such as, but are not limited to, Inception-V3, ResNet18, VGG16, or the architectures disclosed herein.

As described herein, the image diagnostic system 110 can develop a feature extractor based on a convolutional neural network that is trained on the digital pathology database 114, 108. This feature extractor can operate according to the hierarchical histological taxonomy associated with the digital pathology database 114, 108. The architecture of the convolutional neural network disclosed herein can be adapted for processing image patches at a suitable scan resolution and suitable patch size to maintain low computational complexity and high performance accuracy for image-feature transformation, development of data-augmentation methods to compensate for different shortcomings (such as, but not limited to, random effects of rotation, shifting, flipping, and cutting sections of tissue specimen during slide preparation in pathology laboratories, for example), image correction and enhancement techniques for data pre-processing (such as, but not limited to, optical deblurring and color enhancement, for example), and automating the engineering of the convolutional neural network architecture using adaptive techniques of Neural Architecture Search (NAS) methods (such as, but not limited to, searching space, searching strategy, and performance estimation strategy).

The different architectures of the convolutional neural networks can perform differently. For example, the VGG16 architecture can, in some embodiments, perform better than the Inception-V3 and ResNet18 architectures due to the reduced number of layers (i.e., there are 16 layers in VGG16 whereas there are 18 layers in Inception-v3 and 48 layers in ResNet18). It should also be noted that the Inception-V3 architecture is often characterized with a high prediction accuracy and low model complexity, compared to the VGG16 and ResNet18 architectures. The convolutional neural network architectures disclosed herein, in comparison with existing architectures, has a less complex architectural design that can obtain high accuracy predictions and high computational speed.

In some embodiments, the feature extractor can have an architecture consisting of three convolutional blocks, followed by a global max pooling layer, a single fully-connected layer, and a sigmoid layer. Each convolutional block consists of a single convolutional layer, a ReLU activation layer, and a batch normalization layer. Unlike the VGG16 architecture, the sigmoid layer replaces the softmax layer to facilitate multi-label prediction, batch normalization is added after each convolutional layer activation, and a global max pooling layer (which reduces overfitting) replaces the flattening layer since tissues are labeled regardless of their spatial extent. Also, unlike the VGG16 architecture, dropout is used between normalization and convolutional blocks. The batch normalization and dropout are added to regularize the neural network. In contrast to the VGG16 architecture, the architecture of the feature extractor disclosed herein do not include the last two convolutional layers and the two fully connected layers. This difference from the VGG16 architecture can improve classification performance, reduce training time, and increase segmentation resolution.

The feature extractor can generate a feature vector 480 that represents the tissue segments identified in the training image patch at an abstract level.

At 424, the image diagnostic system 110 operates to develop a feature classifier using the training image patches. The feature classifier receives the feature vector 480 from the feature extractor to predict tissue types for the tissue segments identified in the feature vector 480.

The feature classifier can be trainable. For example, the feature classifier can proceed to fit one or more prediction models to establish a mapping between the feature vector 480 and the class confidence scores for the various tissue types available from the training image patches. Example prediction models can include but are not limited to fully-connected (FC) network, support vector machine (SVM), and Statistical Regression.

In some embodiments, the image diagnostic system 110 can develop a non-trainable feature classifier, such as one based on a random-forest technique.

The feature classifier can also generate a class confidence score for each tissue type identified. The confidence score can be continuous-valued. The feature classifier can generate (426) a confidence score vector of a size corresponding to the number of tissue types identified for the feature vector 480.

In some embodiments, the feature classifier can also apply a corresponding confidence threshold to each confidence score to verify the tissue type. For example, when the confidence score associated with the tissue type exceeds or equals a corresponding confidence threshold, the feature classifier can verify the tissue type identified. However, when the feature classifier determines that the confidence score is below the confidence threshold, the feature classifier can indicate that the identified tissue type is incorrect. The verification result can be boolean-valued.

To initiate the classification phase 450, the image diagnostic system 110 receives (460) a whole slide image, such as 500, from the digital pathology scanner 106, or from data storage 114, 108 or the computing device 104. After receiving the whole slide image 500, the image diagnostic system 110 can then divide (462) the whole slide image 500 into one or more image patches 502, and store (464) the image patches 502 into a new image patch database, which can be provided in the data storage 114 and/or the external data storage 108.

In the example shown in FIGS. 7A to 7C, the image diagnostic system 110 divides the whole slide image 500 into nine image patches 502a to 502i. The number of image patches and the region of interest from which the image patches are selected can vary. The image patches 502a to 502i are overlapping in this example embodiment, which can, in some embodiments, improve the quality of the analysis to be conducted by the image diagnostic system 110. The extent of the overlap between each image patch can vary with various factors, such as, characteristics of the whole slide image 500 and the region of interest 501, for example. In some embodiments, the dimension of each image patch 502 can be defined by a number of pixels. The dimension of the image patches 502 can be varied with the applications of the image diagnostic system 110, according to user definitions and/or other factors associated with the use of the image patches 502.

Continuing with reference to FIG. 6, the image diagnostic system 110 operates at 466 to apply the feature extractor developed during the training and validation phase 410 to each of the image patches 502a to 502i. Similar to the process described with respect to 422, the feature extractor then generates a feature vector 482 for each of the image patches 502a to 502i. At 468, the image diagnostic system 110 operates to apply the feature classifier developed during the training and validation phase 410 to each feature vector 482 generated by the feature extractor at 466. Similar to the process described with respect to 424, the feature classifier assigns a tissue type to each tissue segment identified in the feature vector 482 and generates (470) a confidence score for each tissue type identified. The feature classifier can also apply a corresponding confidence threshold to each confidence score to verify the identified tissue type, in some embodiments.

The classification phase 450 can be used as a testing phase by the image diagnostic system 110 to verify the performance of the feature extractor and feature classifier developed at 422 and 424, respectively. For example, the image diagnostic system 110 can use the whole slide image 500 received at 450 as part of a testing dataset.

Figure 8:
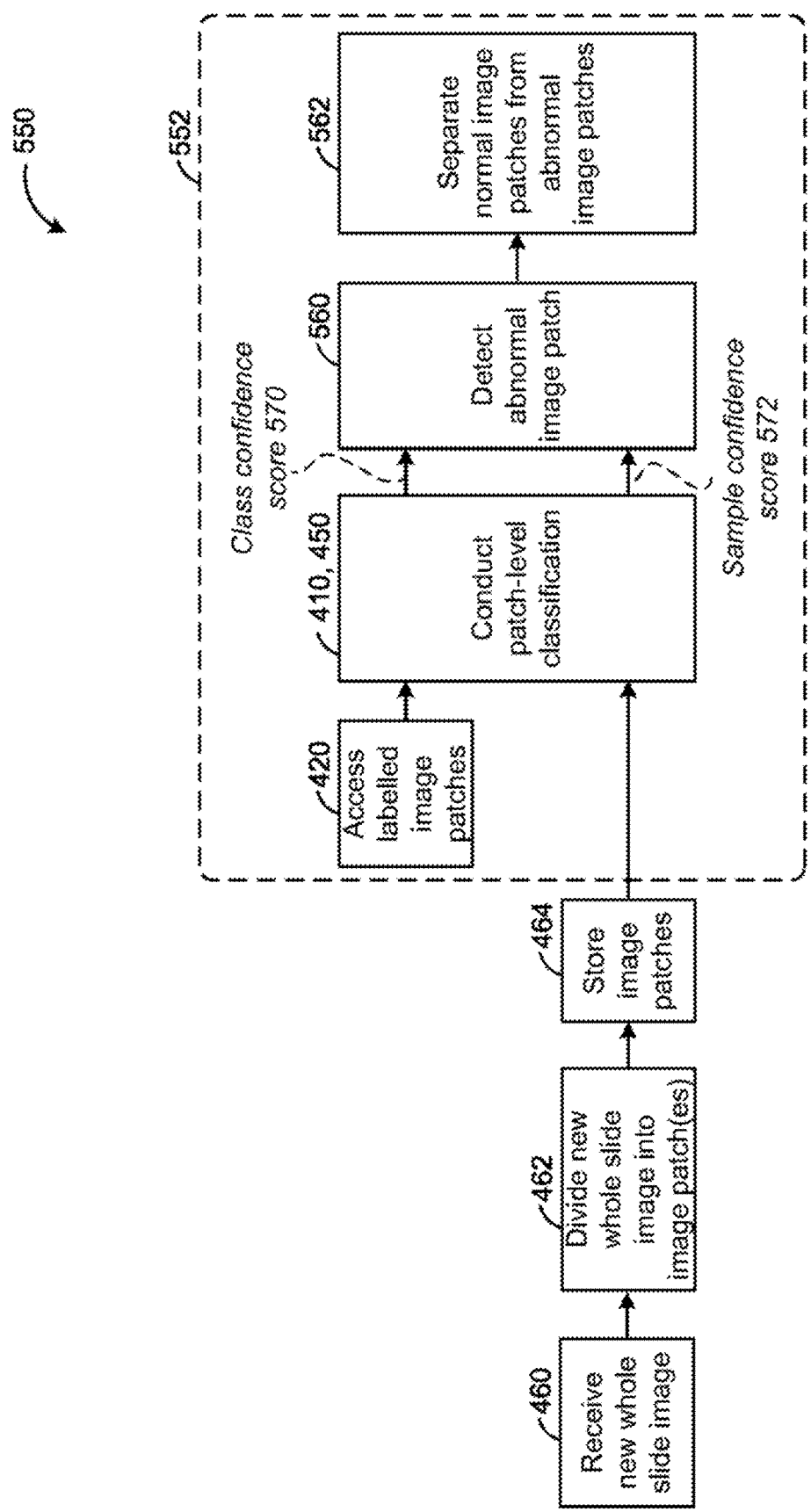
FIG. 8 is a flowchart of an example method of operating the image diagnostic system to identify normal image patches, in accordance with an example embodiment.

Referring now to FIG. 8, which shows a flowchart 550 of an example method of operating the image diagnostic system 110 to identify normal image patches in order to separate normal image patches from abnormal image patches.

The abnormal image patches can include any image patch containing diseased tissues or artifacts (e.g., slide preparation artifacts, such as cross-contamination, an air bubble, and/or a dust speck, and/or tissue-related artifacts, such as a folded tissue, a crushed tissue, a torn tissue, a cut tissue, a cracked tissue, a tissue fixation artifact, and/or a tissue thickness artifact).

Most tissue specimens that a pathologist encounters will likely be healthy specimens. By operating the image diagnostic system 110 to screen for normal image patches and to exclude normal image patches from requiring further review by pathologists, the overall diagnostic process can be reduced significantly. As a result, pathologists can devote their time to diagnosing digital slides containing diseased tissues. Also, the appearances of diseased tissues are highly variable and can be difficult to generalize into certain appearances and structure—even with massive amounts of training dataset related to each type of diseased tissues. For example, the appearance and structure of cancerous tissues are highly variable according to their types and grades.

As shown in FIG. 8, the image diagnostic system 110 can apply the classification method described with reference to FIG. 6 and evaluate (560) the sample confidence score 572 generated by the feature classifier 468 for the image region 501, with reference to the class confidence score 570 generated by the feature classifier 424 for normal image patches to determine whether the identified tissue segment is normal (562). The class confidence score 570 can have a range, in some embodiments.

The sample confidence score 572 generated for the image patch 502 can represent a visual similarity between the sample tissue and the normal tissue. When the image diagnostic system 110 determines that the sample confidence score 572 is within an acceptable range of the class confidence score 570, the image diagnostic system 110 can determine that the sample tissue is normal. However, when the image diagnostic system 110 determines that the sample confidence score 572 is not within the acceptable range of the class confidence score 570, the image diagnostic system 110 can determine that the sample tissue is abnormal and generate a notification requiring further review of the sample tissue by a pathologist. In some embodiments, the image diagnostic system 110 can determine the sample tissue is normal only when the sample confidence score 572 equals or is greater than the class confidence score 570.

The image diagnostic system 110 can also determine whether the whole slide image 500 received at 460 relates to normal tissues. Following 562, the image diagnostic system 110 can group image patches 502 with a high confidence score together and image patches 502 with low confidence scores together. The values of the high confidence scores are compared to the class confidence scores 570 generated by the feature classifier at 424. For example, the high confidence scores can include confidence scores above a confidence threshold and those high confidence scores are averaged and compared with an average of the class confidence scores 570. When the average of the high confidence scores equal or exceed the average of the class confidence scores 570, the image diagnostic system 110 can determine that the whole slide image 500 relates to normal tissues. However, when the average of the high confidence scores is below the average of the class confidence scores 570, the image diagnostic system 110 can determine that the whole slide image 500 relates to abnormal tissues and requires further diagnosis.

Figure 9:
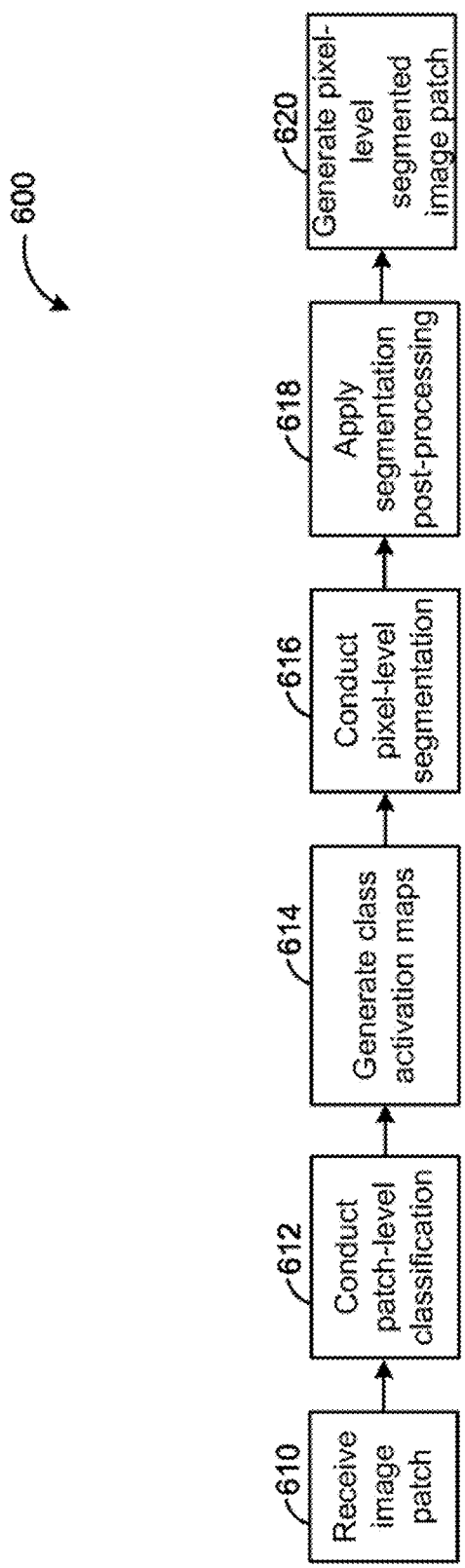
FIG. 9 is a flowchart of an example method of operating the image diagnostic system to generate segmented image patches.

FIG. 9 shows a flowchart 600 of an example method of operating the image diagnostic system 110 to predict pixel-level annotations for the whole-slide images.

With histopathological images, the process of semantic segmentation aims to label each pixel with diagnoses (e.g. cancer or non-cancer), or tissue or cell types (e.g. gland, nuclei, mitotic or non-mitotic). Semantic segmentation approaches for histopathology can be grouped into sliding patch approach, super-pixel approach, pixel-level approach, and weakly-supervised approach.

Sliding patch-based approaches are trained with training datasets and predict at the center pixel of a sliding patch to obtain finer predictions. Convolutional neural networks can be applied in sliding patch-based approaches, and commonly applied for mitosis, cellular, neuronal, and gland segmentation. Sliding patch-based approaches is a type of discriminative localization-based method that uses image-level annotations to generate discriminative object localizations as initial seeds (usually using a convolutional neural network and class activation mapping) and then improve these iteratively.

Super-pixel-based approaches are trained with training datasets and predict latent labels at the super-pixel level. Super-pixel-based approaches are a type of graphical model-based method, which involves extracting regions of homogeneous appearance and predicting latent variable labels from the image level for each region. Convolutional neural networks are typically applied in super-pixel-based approaches to scaled super-pixels for tissue type and nuclear segmentation.

Pixel-based approaches are trained with training datasets and predict at the pixel level and typically apply a fully convolutional network (FCN) with contour separation processing. Fully convolutional network methods can include multi-instance learning-fully convolutional network and Bayesian Fusion of Back Projected Probabilities (BFBP), for example. Pixel-based approaches are example self-supervised based methods, which involve generating interim segmentation masks from image-level annotations and learning pixel-level segmentations from them. Some self-supervised-based methods can iterate between fine and coarse predictions. Other methods produce class activation mappings or saliency maps as initial seeds and refine them to train a fully convolutional network.

Weakly-supervised approaches are trained at the image level and predict at the pixel level. Weakly-supervised approaches tend to involve a patch-based multi-instance learning (MIL) approach. Multi-instance learning based methods typically constrain their optimization to assign at least one pixel per image to each image label. Multi-instance learning based methods can include semantic texton forest (STF), and convolutional neural networks methods like multi-instance learning-inductive logic programming (MIL-ILP) and spatial transformer networks (SPN).

Fully supervised approaches to semantic segmentation, such as sliding patch-based approaches, super-pixel-based approaches and pixel-based approaches, can provide very accurate results because they are trained at the pixel level. However, fully supervised approaches are time-consuming and computationally expensive for labelling digital pathology images at the pixel-level. In contrast, weakly-supervised approaches can train at the patch-level but often provide less accurate results than fully supervised approaches.

Figure 10:
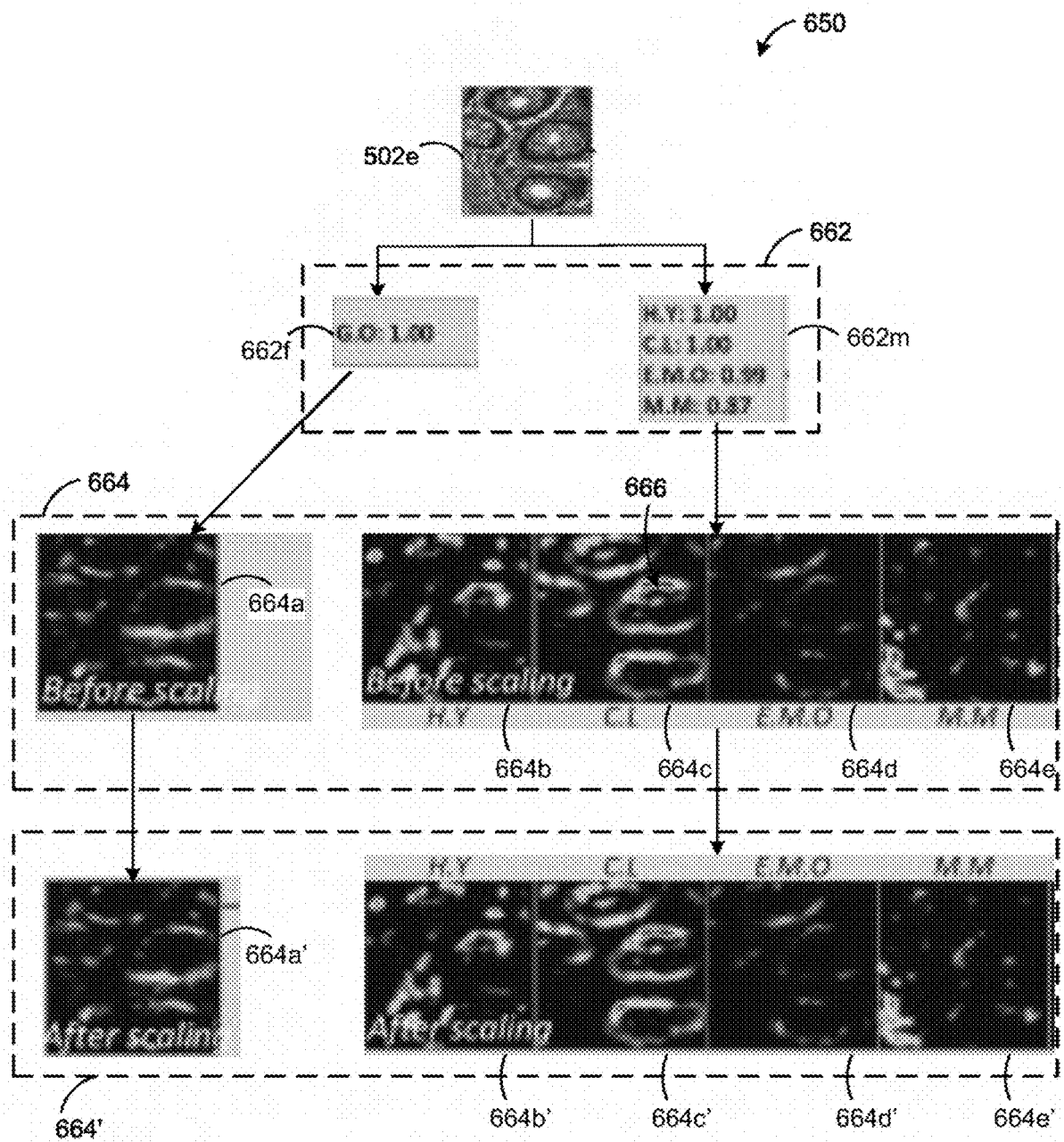
FIG. 10 illustrates the application of the method shown in the flowchart of FIG. 9 to an example image patch.

As will be described with reference to FIG. 9, the image diagnostic system 110 can apply a weakly-supervised approach to semantic segmentation and predict pixel-level labels from the image-level annotations. Reference will be made also to FIG. 10, which illustrates generally at 650 the image diagnostic system 110 applying the method 600 to an example image patch 502e.

At 610, the image diagnostic system 110 receives the image patch 502e. The image diagnostic system 110 then applies the patch-level classification method described with reference to FIG. 6 at 612 to the image patch 502e. The image diagnostic system 110 can generate a feature vector 482 identifying tissue segments within the image patch 502e and tissue types with associated confidence scores for the feature vector 482.

For example, as shown in FIG. 10, example confidence scores 662 corresponding to identified tissue types within the image patch 502e are shown. In this example, for purpose of illustration, the confidence scores for morphological tissue 662m is shown separately from the confidence score for functional tissue 662f.

In respect of the image patch 502e, the image diagnostic system 110 identified four morphological tissues, namely lymphocytes tissue (H.Y.), loose connective tissue (C.L.), simple columnar epithelial tissue (E.M.O.), and smooth muscle tissue (M.M.), and one functional tissue, namely exocrine gland tissue (G.O.). The image diagnostic system 110 also generated a corresponding confidence score for each of the identified tissue, as generally illustrated at 662m and 662f. The image diagnostic system 110 assigned a confidence score of 1.00 for lymphocytes tissue (H.Y.), a confidence score of 1.00 for loose connective tissue (C.L.), a confidence score of 0.99 for simple columnar epithelial tissue (E.M.O.), a confidence score of 0.87 for smooth muscle tissue (M.M.), and a confidence score of 1.00 for exocrine gland tissue (G.O.).

Figure 11B:
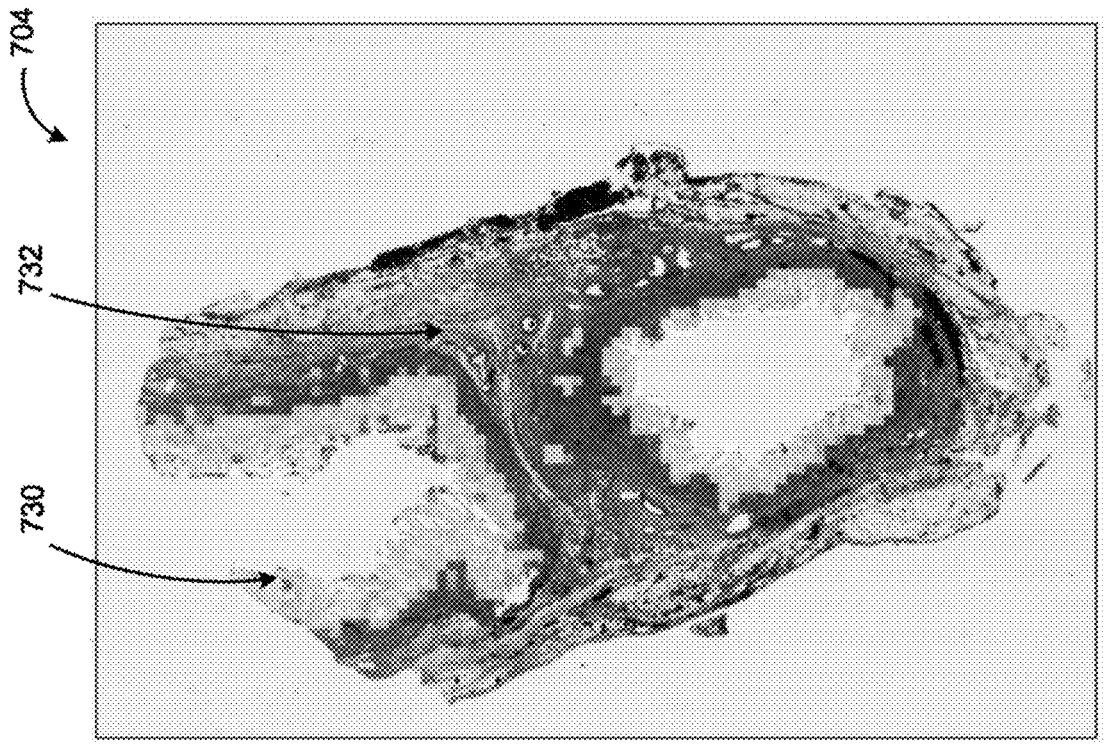
FIG. 11B shows another example class activation map corresponding to the digital slide represented in FIG. 11A.
Figure 11A:
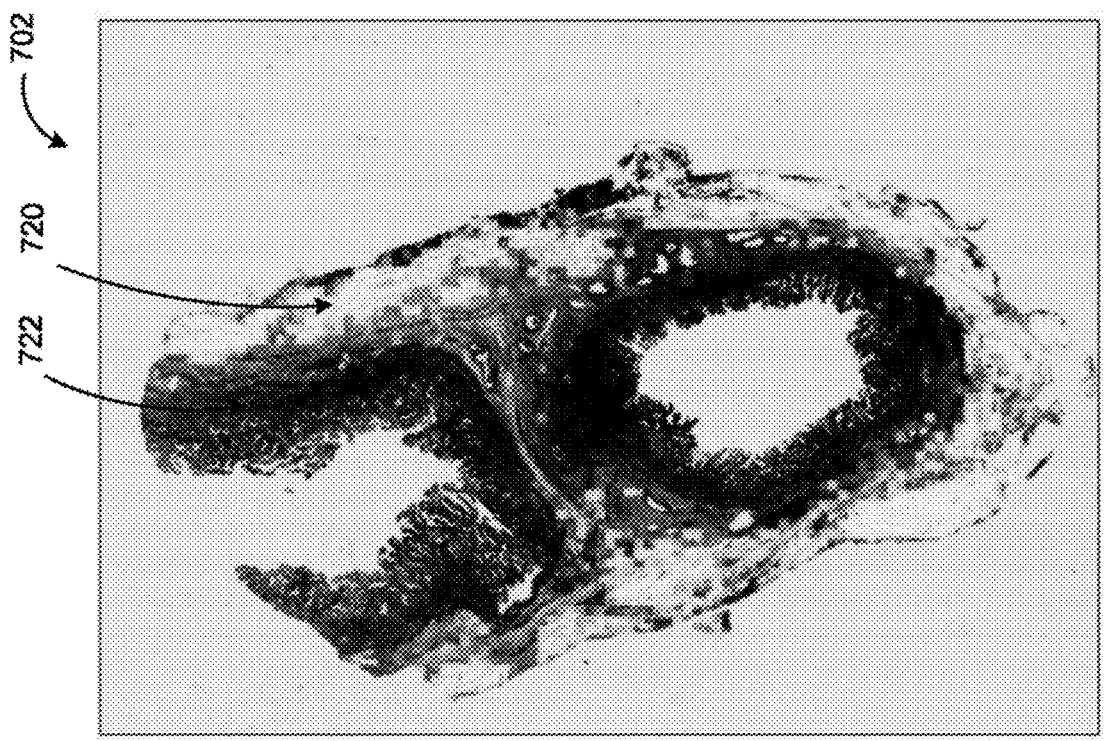
FIG. 11A shows an example class activation map for an example digital slide.

At 614, the image diagnostic system 110 generates a class activation map (CAM) based on the feature vector 482 and confidence score vector 662 generated at 610. The class activation map can provide a visual representation of the confidence scores generated by the feature classifier without requiring the tissue type labels. Instead, the tissue types can be identified with different visual representations, for example, such as different colours or shading. FIGS. 11A and 11B illustrate example class activation maps for a digital slide.

FIG. 11A shows an example class activation map 702 for a digital slide. The example class activation map 702 illustrates the tissue types assigned a confidence score equal to or greater than 95%. Other confidence thresholds can be applied, depending on the application of the image diagnostic system 110. The areas in light grey correspond to white adipose tissues, while the areas in dark grey correspond to non-descriptive tissues. The area referenced generally at 720 corresponds mostly to white adipose tissues (mostly light grey), whereas the area referenced generally at 722 corresponds mostly to non-descriptive tissues (mostly dark grey).

FIG. 11B shows another example class activation map 704 for the same digital slide represented in FIG. 11A. Similar to class activation map 702, class activation map 704 illustrates the tissue types assigned a confidence score equal to or greater than 95%. The areas in light grey correspond to exocrine gland tissues, while the areas in dark grey correspond to non-descriptive tissues. The area referenced generally at 730 corresponds mostly to exocrine glad tissues (mostly light grey), and the area referenced generally at 732 corresponds mostly to non-descriptive tissues (mostly dark grey).

The class activation map can, in some embodiments, include a pixel-level class activation map that can indicate, at the pixel level, the section of the image patch 502e that contributed to the respective confidence score 662. The pixel-level interpretation of the confidence scores, in contrast to labels, can be more helpful for visualizing the tissues.

The image diagnostic system 110 can apply a gradient-class activation map (Grad-CAM) method, which is a weakly-supervised semantic segmentation (WSSS) method that generalizes the class activation map method. In some embodiments, the gradient-class activation map method can be a gradient-weighted class activation map method. The gradient-class activation map method, in comparison to similar weakly-supervised semantic segmentation methods, is simpler as no re-training is required and more versatile as it can be applied to any convolutional neural network architecture.

In some embodiments, the image diagnostic system 110 can vary the method with which the pixel-level class activation maps are generated for different tissue types. For example, the image diagnostic system 110 can vary the gradient-class activation maps method to account for different characteristics of morphological tissues and functional tissues.

For example, referring again to FIG. 10, example pixel-level class activation maps are illustrated generally at 664. The image diagnostic system 110 generates pixel-level class activation map 664a for exocrine gland tissue (G.O.), pixel-level class activation map 664b for lymphocytes tissue (H.Y.), pixel-level class activation map 664c for loose connective tissue (C.L.), pixel-level class activation map 664d for simple columnar epithelial tissue (E.M.O.), and pixel-level class activation map 664e for smooth muscle tissue (M.M.). Example scaled pixel-level class activation maps 664a' to 664e' are shown in FIG. 10 as well. In some embodiments, the image diagnostic system 110 can scale the class activation maps 664 to further distinguish the confident scores of interest.

For illustrative purposes, an area generally illustrated at 666 in the pixel-level class activation map 664c can be seen to have contributed to the confidence score generated by the feature classifier for loose connective tissue (C.L.) within the image patch 502e. Area 666 is illustrated only as an example and as can be seen from the pixel-level class activation map 664c, other areas not specifically identified herein also contributed to the confidence score generated by the feature classifier.

At 616, the image diagnostic system 110 conducts pixel-level segmentation on the pixel-level class activation maps 664a to 664e generated at 614 to outline tissue segments at each pixel of the image patch 502e. The image diagnostic system 110 can outline the contour of each tissue segment within each pixel-level class activation maps 664a to 664e.

Figures 12A, 12B, 12C:
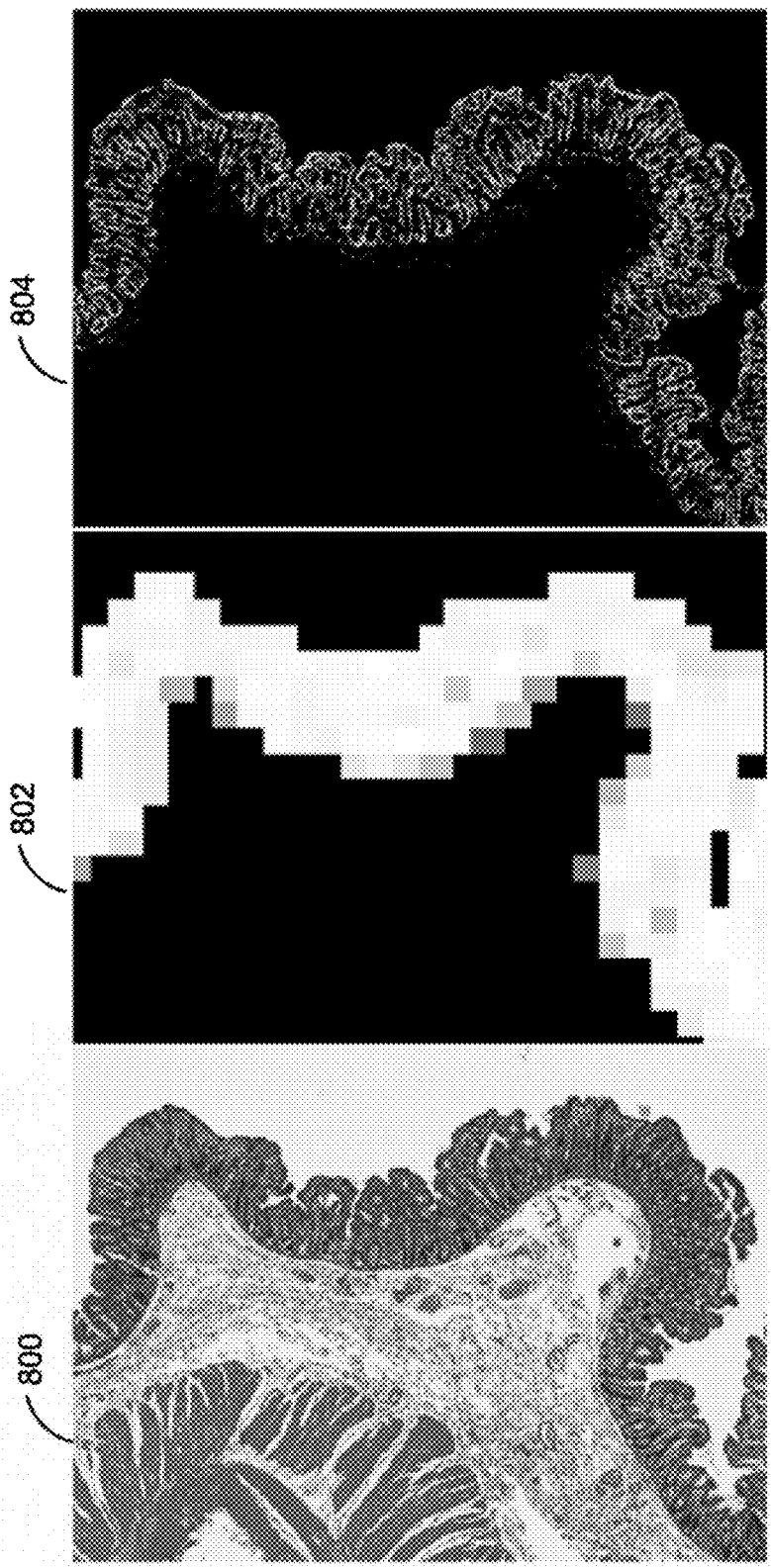
FIG. 12A is an example region of interest.
FIG. 12B is an example class activation map for the region of interest shown in FIG. 12A.
FIG. 12C is an example segmented image corresponding to the region of interest shown in FIG. 12A.

FIGS. 12A to 12C illustrates another example. FIG. 12A illustrates an example region of interest 800. After the image diagnostic system 110 analyzes the region of interest 800 at 612, the image diagnostic system 110 can generate a class activation map 802 (at 614) representing the confidence scores assigned to regions identified as simple columnar epithelial tissues. Based on the class activation map 802, the image diagnostic system 110 can conduct pixel-level segmentation to outline the tissue segments to generate a segmented image patch 804. From comparing FIG. 12B with FIG. 12C, the pixel-level segmentation conducted at 616 can result in finer details and shapes that are lost at the patch-level identification at 612.

The image diagnostic system 110 can further adjust the pixel-level class activation maps 664 generated at 614.

The digital pathology database 114, 108 on which the training dataset is stored typically does not include any image data with non-tissue labels. When the image diagnostic system 110 analyzes the image patch 502e, the image diagnostic system 110 can produce a background class activation map corresponding to the background for both morphological and functional tissue analyses, and a non-tissue class activation map corresponding to non-tissue characteristics for functional tissue analysis. The image diagnostic system 110 can then apply the background and non-tissue class activation maps to each of the tissue class activation maps to avoid making pixel predictions where no such tissue type exists within the digital pathology database 114, 108.

In digital pathology images, background pixels are typically associated with high intensity values (i.e. they appear white in the image), except for tissues that stain transparent, such as white adipose and brown adipose tissues, and exocrine glandular, endocrine glandular, and transport vessels tissues. To generate the background class activation map, the image diagnostic system 110 can apply a scaled-and-shifted sigmoid to a mean-RGB image to generate a smoothed high intensity background image. The image diagnostic system 110 can then subtract the appropriate transparent staining class activation maps from the smoothed high intensity background image to generate the background class activation map. The image diagnostic system 110 can apply a filter, such as a 2-dimensional Gaussian blur $H_{\mu,\sigma}$, to reduce the prediction resolution.

For non-tissue class activation map corresponding to non-tissue characteristics of functional tissues, non-functional pixels generally correspond to low confidence scores. The image diagnostic system 110 can generate a non-functional tissue class activation map corresponding to tissue pixels without a functional role. To generate this non-functional tissue class activation map, the image diagnostic system 110 can subtract the functional tissue class activation maps from the two-dimensional maximum of the other functional class activation maps, the class activation maps for white and brown adipose tissues, and the background class activation map. The image diagnostic system 110 can also scale the resulting non-functional tissue class activation map.

At 618, the image diagnostic system 110 can apply segmentation post-processing to the identified tissue segments to increase visual homogeneity. The resultant class-specific gradient-class activation maps (CSGCs) at 616 can include predictions that poorly conform to object contours. In some embodiments, the post-processing can involve applying a fully-connected conditional random field (CRF) modeling method.

Figures 13A, 13B, 13C:
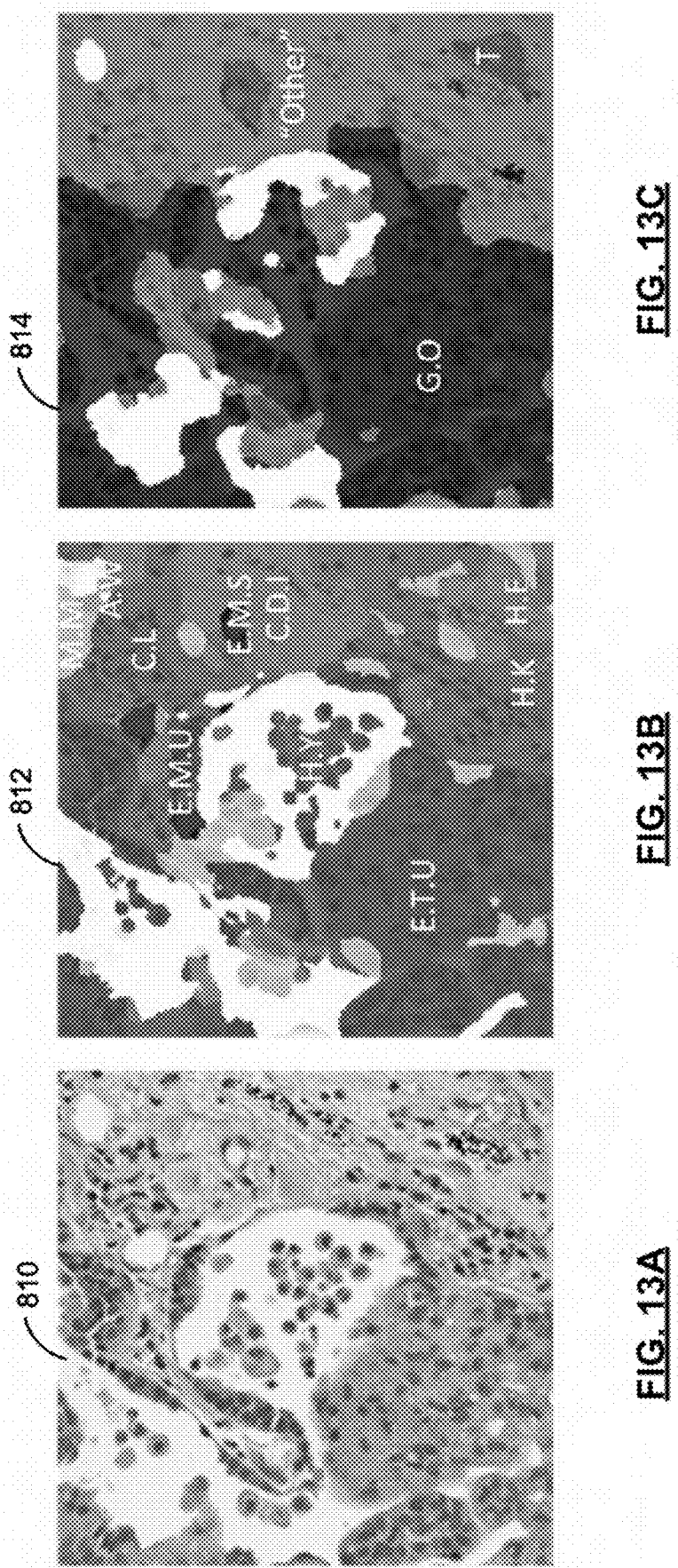
FIG. 13A is another example image patch.
FIG. 13B is an example segmented image patch corresponding to the image patch of FIG. 13A.
FIG. 13C is another example segmented image patch corresponding to the image patch of FIG. 13A.

At 620, the image diagnostic system 110 can generate pixel-level segmented image patches. Reference will now be made to FIGS. 13A to 13C.

FIG. 13A illustrates an example image patch 810. The image diagnostic system 110 applies the method 600 to example image patch 810 and generates the segmented image patches 812 of FIG. 13B and 814 of FIG. 13C. The segmented image patch 812 illustrates identified morphological tissues outlined and labeled, and the segmented image patch 814 illustrates identified functional tissues outlined and labeled. The labels may not be necessary as other visual aids can be used to identify the tissue types, such as colour code (which is also used in segmented image patches 812 and 814) or shading.

Figures 14A, 14B:
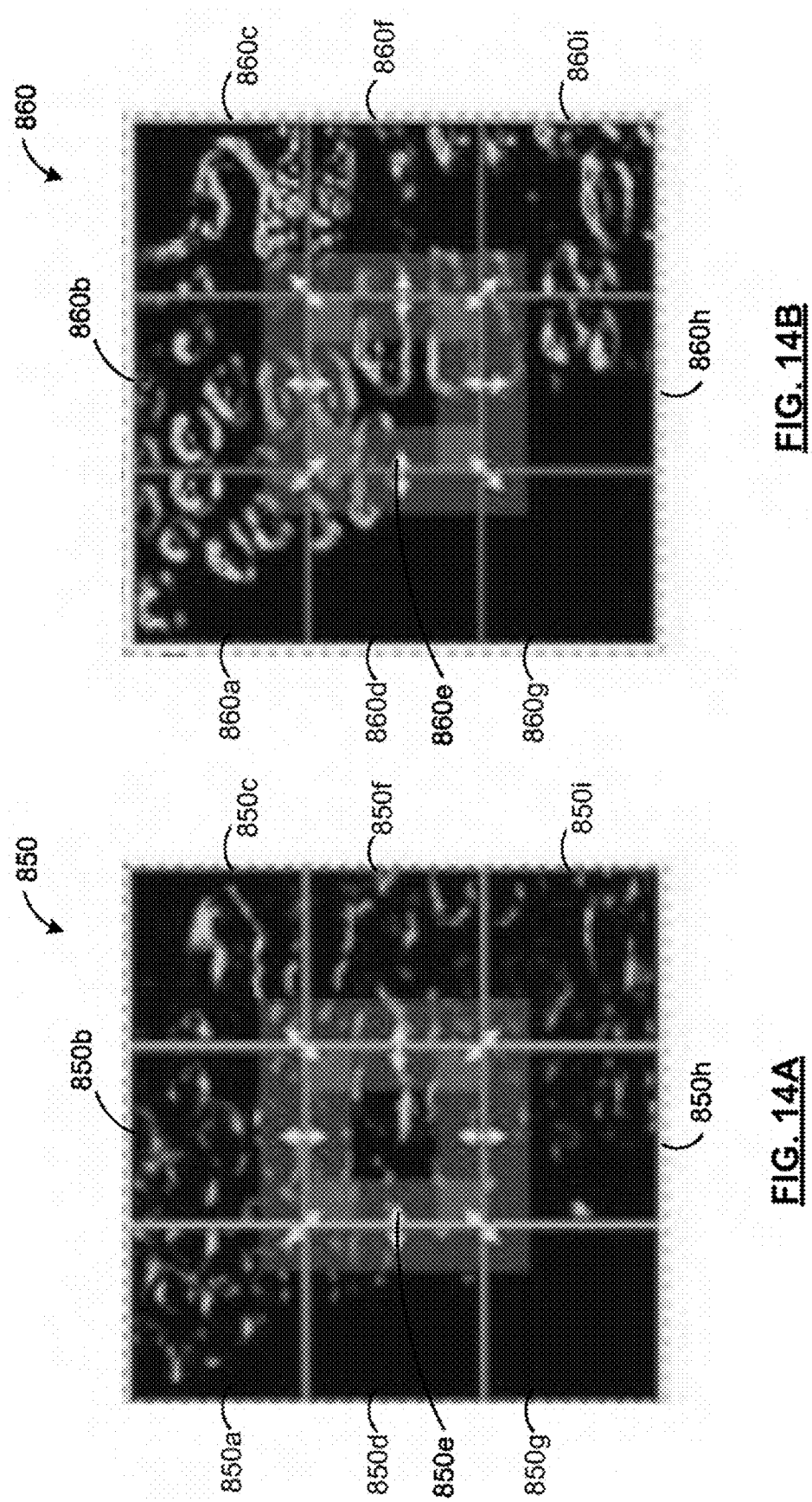
FIG. 14A shows example class activation maps corresponding to the image patches of FIG. 7C.
FIG. 14B shows another example class activation maps corresponding to the image patches of FIG. 7C.

For illustrative purposes, the method 600 is described with reference to the image patch 502e of FIG. 7C. The image diagnostic system 110 can also apply the method 600 to each of the other image patches 502a to 502d and 502f to 502i. FIGS. 14A and 14B illustrate corresponding class activation maps 850 and 860 for the image patches 502 for specific tissue types. FIG. 14A illustrates corresponding class activation maps 850a to 850i for the loose connective tissues (C.L.) and FIG. 14B illustrates corresponding class activation maps 860a to 860i for the exocrine gland tissues (G.O.).

When stitching together each set of the class activation maps 850, 860, the image diagnostic system 110 can average the overlapping areas.

Figure 15:
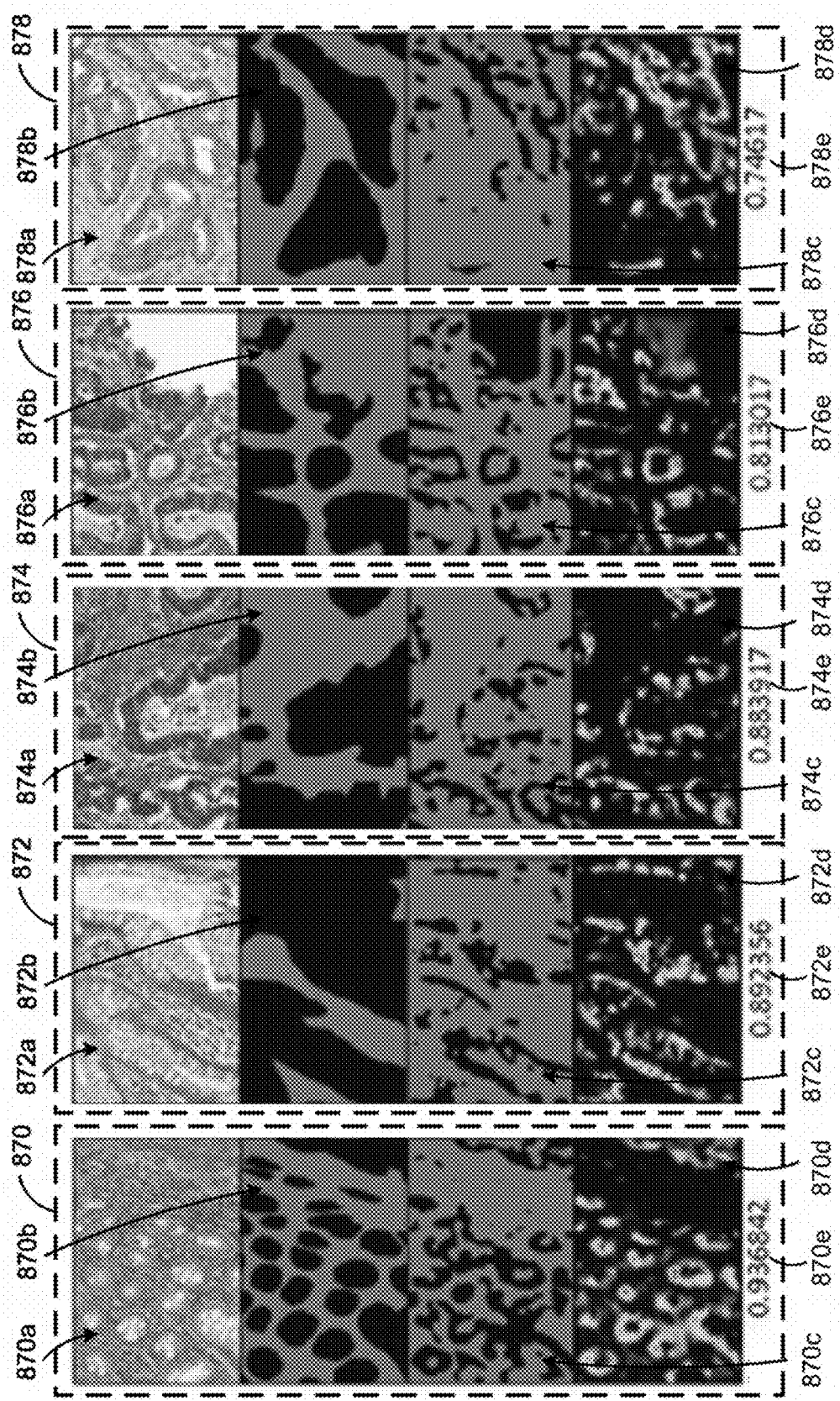
FIG. 15 illustrates example results generated by the image diagnostic system for exocrine gland tissues of different health states, in accordance with an example embodiment.

FIG. 15 illustrates example results from operating the image diagnostic system 110 to conduct method 600 on image patches of exocrine gland tissues of different health.

The example illustrated at 870 relates to an image patch 870a of healthy exocrine gland tissues. The examples illustrated at 872 to 878 relate to respective image patches 872a to 878a of exocrine gland tissues of worsening health. Example 872 relates to adenomatous exocrine gland tissues, example 874 relates to moderately differentiated exocrine gland tissues, example 876 relates to poorly-to-moderated differentiated exocrine gland tissues, and example 878 relates to poorly differentiated exocrine gland tissues.

Images 870b, 872b, 874b, 876b, 878b represent the training segmented image patches. As the exocrine gland tissue worsens in health (from 870b to 878b), the contour of the exocrine gland tissue becomes increasing misshapened.

Images 870c, 872c, 874c, 876c, 878c represent the segmented image patches and image 870d, 872d, 874d, 876d, 878d represent the respective class activation maps generated from operating the image diagnostic system 110 to conduct method 600 to respective image patches 870a, 872a, 874a, 876a, 878a. As the exocrine gland tissue worsens in health (from 870c to 878c), the image diagnostic system 110 generates segmented image patches 870c, 872c, 874c, 876c, 878c and class activation maps 870d, 872d, 874d, 876d, 878d that are increasingly dissimilar in comparison with the training segmented image patches 870b, 872b, 874b, 876b, 878b. Similarly, the respective confidence scores 870e, 872e, 874e, 876e, 878e decrease in value with the worsening exocrine gland tissue.

Figure 16:
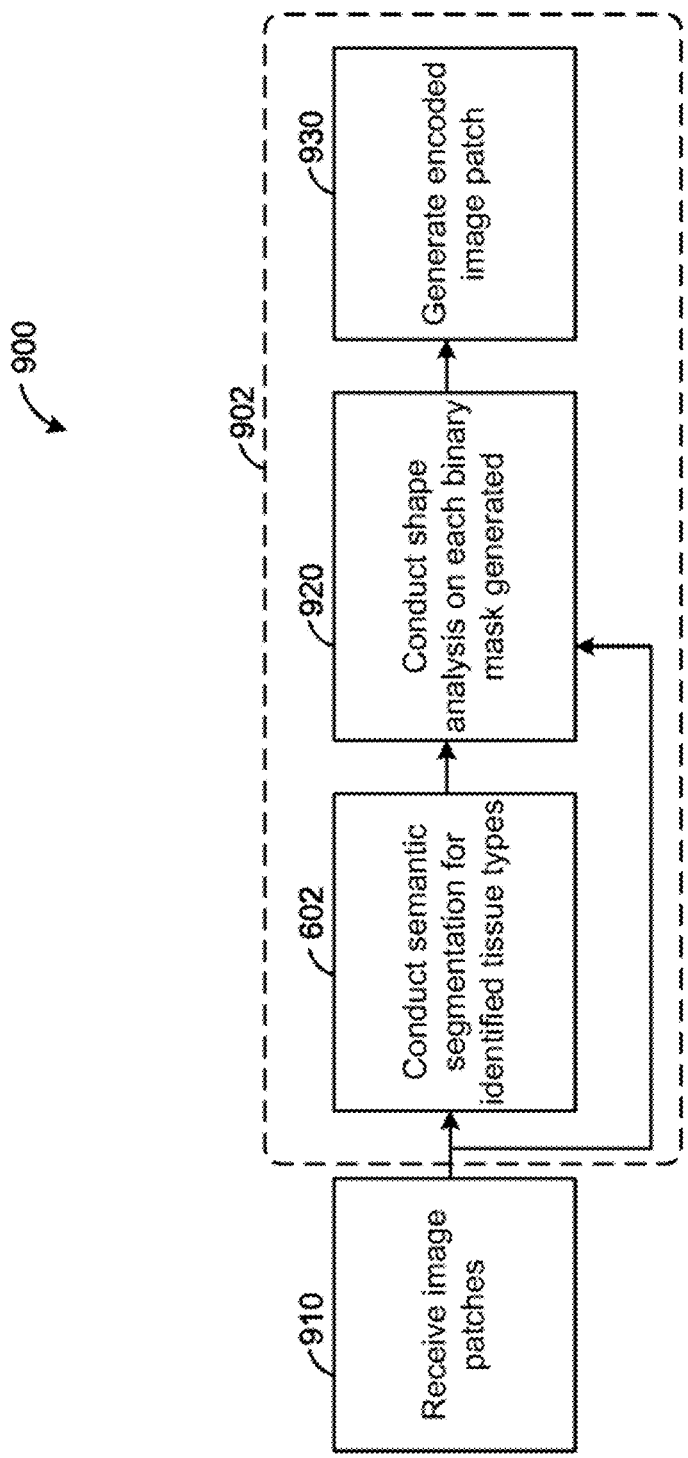
FIG. 16 is a flowchart of an example method of operating the image diagnostic system to generate encoded image patches, in accordance with an example embodiment.

Referring now to FIG. 16, which shows a flowchart 900 of an example method of operating the image diagnostic system 110 to generate encoded image patches.

At 910, the image diagnostic system 110 can receive an image patch, such as image patch 502e.

The image diagnostic system 110 can apply the method 602 to the image patch 502e to conduct semantic segmentation to outline the various tissue segments identified therein. From applying the method 602, the image diagnostic system 110 can generate binary masks corresponding to each identified tissue type. Each binary mask corresponds to pixel-level representations of the tissue segments of the identified tissue type within the image patch.

At 920, the image diagnostic system 110 conducts a feature analysis of each binary mask to extract features related to the relevant tissue segment within the binary mask. Example features can include geometrical features related to the structure of the relevant tissue, such as shape (e.g., elongated, rectangular, tubular, circular, blob-like, etc.), and features related to the original image in the same image area associated with the identified shapes (e.g., statistical feature measures like gray-level and standard deviation, edge image features information, etc.). For example, if the image diagnostic system 110 detects a blob shape, the image diagnostic system 110 can also extract features related the image features inside the blob available from the original image. These features can be used by the image diagnostic system 110 to account for gray level image features, for example. In some embodiments, the image diagnostic system 110 can obtain the image patch 502e also when conducting 920.

At 930, the image diagnostic system 110 generates the encoded image patch for the image patch 502e based on the features identified at 920 for each binary mask.

Figure 17:
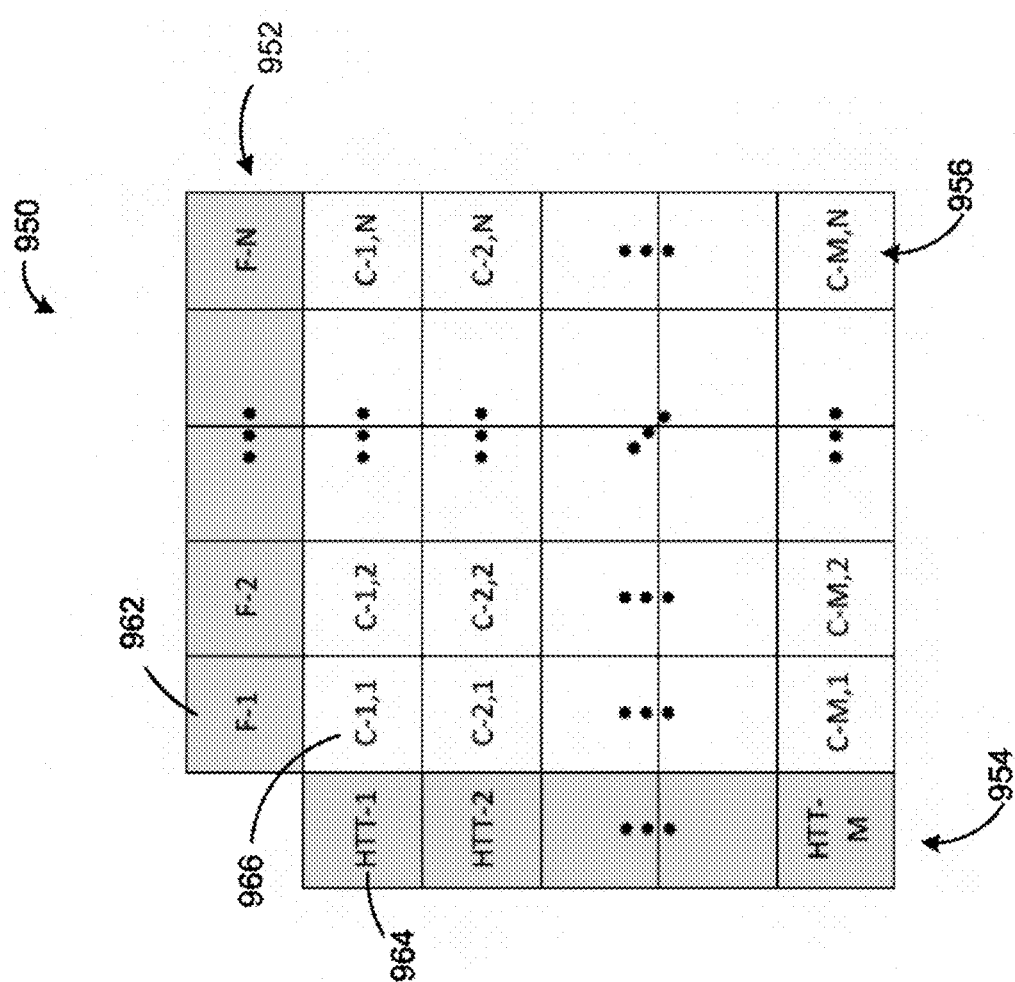
FIG. 17 shows an example representation of an encoded image patch, in accordance with an example embodiment.

FIG. 17 illustrates an example representation of an encoded image patch 950. The encoded image patch 950 includes feature correspondence values 956 that indicate how similar a structure of a tissue type is to a feature identified at 920. In this example, the encoded image patch 950 can be represented with a matrix with the columns 952 corresponding to the features identified at 920 and the rows 954 corresponding to the tissue types identified by the feature classifier. Feature correspondence value 966, for example, indicates how similar the structure of the tissue type 964 is to the feature 962.

In some embodiments, the image diagnostic system 110 can generate the encoded image patch 950 for each hierarchy level defined in hierarchical histological taxonomy used for labelling the image patch 502e. For example, when the hierarchical histological taxonomy 280 is used for labelling the image patch 502e, an encoded image patch 950 can be generated for each hierarchical level 290, 292, and 294 so that the image patch 502e can be represented by three different encoded image patches 950. The encoded image patches 950 for the different hierarchical levels 290, 292, and 294 can be aggregated, in some embodiments.

The encoded image patch 950 can be an abstract representation of the tissue characteristics within the image patch 502*e*. By encoding the image patches 502 based on characteristics of the tissue, the encoded image patch 950 will include essential features of interest and minimal redundant information. This can facilitate comparison between image patches 502 and searching by the image diagnostic system 110 for specific features within the stored image patches 502. For example, the image diagnostic system 110 can receive search parameters defining specific tissue features of interest and can then identify from the encoded image patches 950 stored in the data storage 114, 108 the image patches 502 that satisfy the search parameters.

Figure 18:
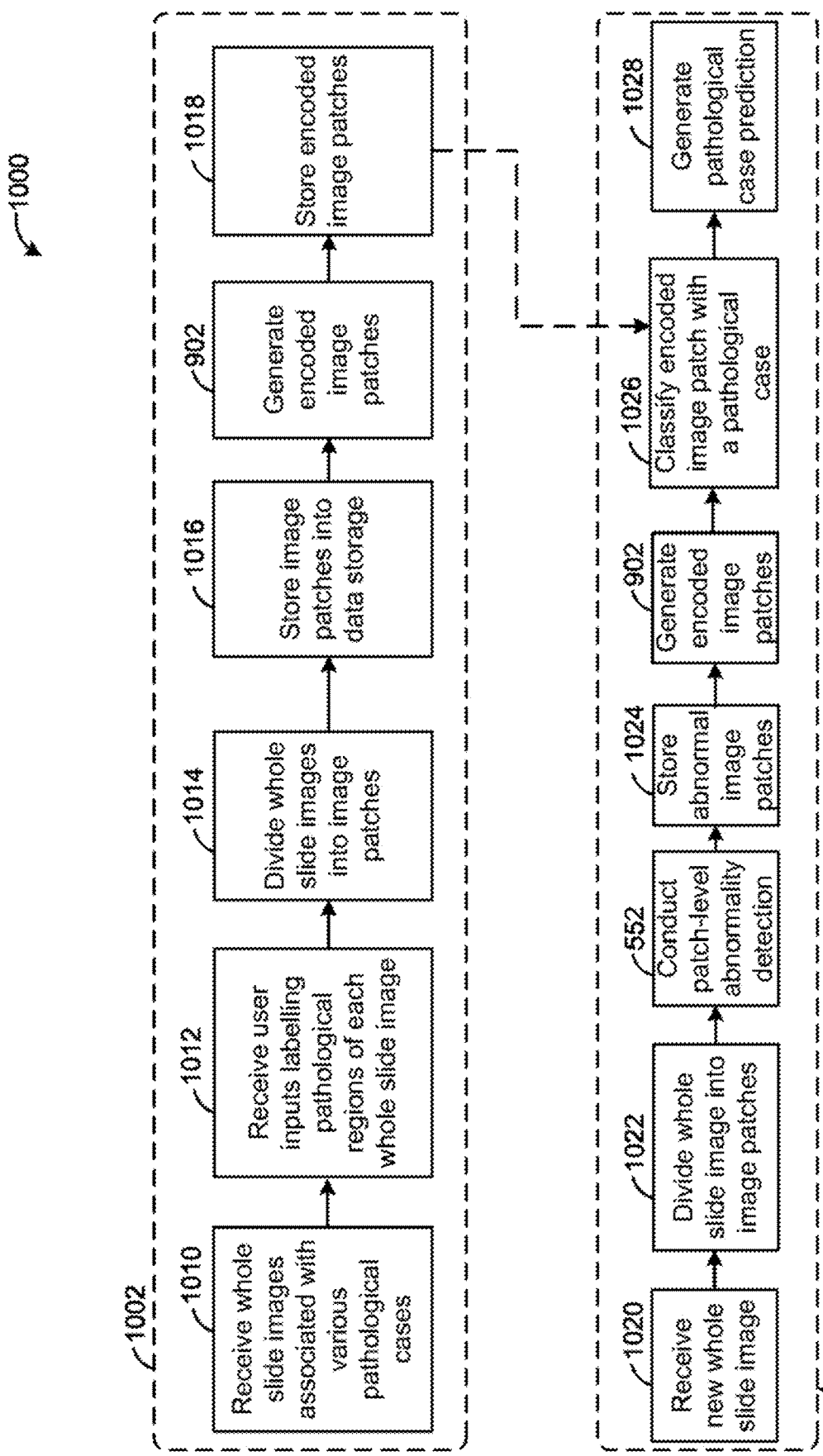
FIG. 18 is a flowchart of an example method of operating the image diagnostic system to diagnose image patches with a pathological case, in accordance with an example embodiment.

FIG. 18 shows a flowchart 1000 of an example method of operating the image diagnostic system 110 to classify image patches 502 as different pathological cases, or diseases. Certain diseased tissues can be characterized by unique tissue arrangements in comparison with normal tissues. The image diagnostic system 110 can analyze image patches based on a structural analysis of specific tissues to generate a disease diagnosis.

The method 1000 involves a pathological case database construction phase 1002 and a pathological case classification phase 1004.

During the pathological case database construction phase 1002, the image diagnostic system 110 can receive (1010) whole slide images of various pathological cases and receive (1012) user inputs that labels regions associated with specific pathological cases within the whole slide images. The image diagnostic system 110 can provide a user interface from which the user inputs can be received. The user inputs can be received from experienced histology labeling experts, such as board-certified pathologists, who are trained to recognize tissues according to the hierarchical histological taxonomy 280.

The image diagnostic system 110 can then divide each labelled whole slide image into multiple image patches. In some embodiments, the image diagnostic system 110 can identify the labelled regions and generate image patches for the labelled regions to reduce unnecessary computation.

At 1016, the image diagnostic system 110 organizes the image patches by the associated pathological case and stores the image patches associated with the same pathological case in association with each other and in association with the identified pathological case. For example, the image diagnostic system 110 can store image patches associated with the same pathological case in separate, dedicated databases provided by the data storage 114, 108.

The image diagnostic system 110 then generates an encoded image patch 950 according to the method 902 for each image patch stored at 1016. The image diagnostic system 110 then stores (1018) each encoded image patch 950 associated with the same pathological case in association with each other and in association with the identified pathological case. As with the storage of image patches at 1016, the image diagnostic system 110 can store the encoded image patches 950 associated with the same pathological case in separate, dedicated databases provided by the data storage 114, 108. The stored encoded image patches 950 can be used by the image diagnostic system 110 as a pathological databank for different pathological cases.

The image diagnostic system 110 can then use the pathological databank to diagnose new whole scan images for pathological cases. For example, at 1020, the image diagnostic system 110 can receive a new whole scan image and can then divide the whole scan image into image patches at 1022. The image diagnostic system 110 applies the method 552 to each image patch to separate normal image patches from abnormal image patches. At 1024, the image diagnostic system 110 stores the identified abnormal image patches in the data storage 114, 108. The identified abnormal image patches can be stored in a separate, dedicated databases provided by the data storage 114, 108, in some embodiments.

The image diagnostic system 110 can then conduct the method 902 for each image patch stored at 1024 to generate a respective encoded image patch. The image diagnostic system 110 can then compare (1026) each encoded image patch generated at 902 with the information available in the pathological databank constructed at 1002 to generate (1028) a pathological case prediction.

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers (referred to below as computing devices) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Various embodiments have been described herein by way of example only. Various modification and variations may be made to these example embodiments without departing from the spirit and scope of the invention, which is limited only by the appended claims.

We claim:

1. A system for generating a pixel-level segmented image patch for an image patch, the system comprises a processor operable to:
    apply a developed feature extractor to the image patch to identify one or more tissue segments within the image patch;
    apply a developed feature classifier to the one or more tissue segments to identify a respective tissue type and generate a corresponding confidence score representing a degree of similarity according to at least one prediction model generated based on a set of training image patches of a normal tissue of that tissue type, the tissue type being identified according to a hierarchical histology taxonomy;
    generate a class activation map for each identified tissue type based on the associated confidence score; and
    apply pixel-level segmentation to the class activation map to define a contour of each tissue segment of that tissue type to generate the pixel-level segmented image patch.

2. The system of claim 1, wherein the processor is operable to apply a gradient-class activation map (Grad-CAM) method to generate the class activation map.

3. The system of claim 1, wherein the processor is operable to:
    determine one or more tissue characteristics of the tissue type; and
    generate the class activation map based on the one or more tissue characteristics.

4. The system of claim 3, wherein the one or more tissue characteristics comprises one of a morphological tissue type and a functional tissue type.

5. The system of claim 1, wherein the class activation map comprises a pixel-level class activation map.

6. The system of claim 1, wherein the processor is operable to apply one or more post-processing techniques to the class activation map to increase a visual homogeneity of each tissue type segment.

7. The system of claim 6, wherein the one or more post-processing techniques comprises a fully-connected conditional random field (CRF) modeling method.

8. The system of any claim 1, wherein the processor is operable to adjust the class activation map with a background class activation map generated based on image data associated with high white-illumination values.

9. The system of claim 1, wherein the processor is operable to adjust the class activation map associated with a functional tissue type with a non-tissue class activation map generated based on image data associated with non-tissue characteristics.

10. The system of claim 1, wherein:
    the system further comprises a supervised digital pathology database having a set of training image patches stored thereon; and
    the processor is operable to:
        receive one or more image patches of normal tissue;
        receive, via a labelling user interface, one or more user inputs to label each image patch with at least one tissue type according to a hierarchical histological taxonomy; and
        store each labelled image patch in the supervised digital pathology database.

11. The system of claim 10, wherein the processor is in communication with the supervised digital pathology database and operable to:
    access the set of training image patches stored in the supervised digital pathology database;
    develop a feature extractor to generate a training feature vector identifying one or more training tissue segments in each training image patch in the set of training image patches; and
    develop a feature classifier to assign a tissue type to each training tissue segment identified in the training feature vector and to update a class confidence score for that tissue type, the tissue type being assigned according to the hierarchical histological taxonomy.

12. The system of claim 10, wherein the processor is in communication with the supervised digital pathology database and operable to:
    develop a convolutional neural network based on the set of training image patches.

13. A method for generating a pixel-level segmented image patch for an image patch, the method comprises operating a processor to:
    apply a developed feature extractor to the image patch to identify one or more tissue segments within the image patch;
    apply a developed feature classifier to the one or more tissue segments to identify a respective tissue type and generate a corresponding confidence score representing a degree of similarity according to at least one prediction model generated based on a set of training image patches of a normal tissue of that tissue type, the tissue type being identified according to a hierarchical histology taxonomy;

generate a class activation map for each identified tissue type based on the associated confidence score; and apply pixel-level segmentation to the class activation map to define a contour of each tissue segment of that tissue type to generate the pixel-level segmented image patch.

14. The method of claim 13, comprises operating the processor to apply a gradient-class activation map (Grad-CAM) method to generate the class activation map.

15. The method of claim 13 comprises operating the processor to:

determine one or more tissue characteristics of the tissue type; and generate the class activation map based on the one or more tissue characteristics.

16. The method of claim 15, wherein the one or more tissue characteristics comprises one of a morphological tissue type and a functional tissue type.

17. The method of claim 13, wherein the class activation map comprises a pixel-level class activation map.

18. The method of claim 13 comprises operating the processor to apply one or more post-processing techniques to the class activation map to increase a visual homogeneity of each tissue type segment.

19. The method of claim 18, wherein the one or more post-processing techniques comprises a fully-connected conditional random field (CRF) modeling method.

20. The method of claim 13 comprises operating the processor to adjust the class activation map with a background class activation map generated based on image data associated with high white-illumination values.

21. The method of claim 13 comprises operating the processor to adjust the class activation map associated with a functional tissue type with a non-tissue class activation map generated based on image data associated with non-tissue characteristics.

22. The method of claim 13 comprises operating the processor to:

receive one or more image patches of normal tissue;

receive, via a labelling user interface, one or more user inputs to label each image patch with at least one tissue type according to a hierarchical histological taxonomy; and store each labelled image patch in a supervised digital pathology database having a set of training image patches stored thereon.

23. The method of claim 22 comprises operating the processor to:

access the set of training image patches stored in the supervised digital pathology database;

develop a feature extractor to generate a training feature vector identifying one or more training tissue segments in each training image patch in the set of training image patches; and develop a feature classifier to assign a tissue type to each training tissue segment identified in the training feature vector and to update a class confidence score for that tissue type, the tissue type being assigned according to the hierarchical histological taxonomy.

24. The method of claim 22 comprises operating the processor to:

develop a convolutional neural network based on the set of training image patches.

25. A system for generating an encoded image patch for an image patch of at least one tissue, the system comprises a processor operable to:

apply a developed feature extractor to the image patch to identify one or more tissue segments within the image patch;

apply a developed feature classifier to the one or more tissue segments to identify a respective tissue type and generate a corresponding confidence score representing a degree of similarity according to at least one prediction model generated based on a set of training image patches of a normal tissue of that tissue type, the tissue type being identified according to a hierarchical histology taxonomy;

generate a class activation map for each identified tissue type based on the associated confidence score;

apply pixel-level segmentation to the class activation map to define a contour of each tissue segment of that tissue type to generate the pixel-level segmented image patch;

generate one or more binary masks for the image patch, each binary mask being associated with an identified tissue type and corresponding to a pixel-level representation of one or more tissue segments of that tissue type;

for each binary mask, identify one or more features related to a structure of each tissue segment;

generate one or more feature correspondence values relating each feature identified in each binary mask and each tissue type identified for the image patch; and generate the encoded image patch based on the one or more feature correspondence values.

26. The system of claim 25, wherein the processor is operable to generate the feature correspondence value to represent a similarity of a structure of a tissue segment to a feature of the one or more features.

27. The system of claim 25, wherein the encoded image patch comprises a matrix of the one or more feature correspondence values with a number of columns corresponding to a number of unique features identified in the one or more binary masks and a number of rows corresponding to a number of unique tissue types identified for the image patch.

28. The system of 25, wherein the processor is operable to generate a unique encoded image patch for each hierarchy level of the hierarchical histological taxonomy based on which the one or more tissue types are identified.

29. The system of claim 28, wherein the processor is operable to aggregate each unique encoded image patch to generate an aggregated encoded image patch.

30. A method for generating an encoded image patch for an image patch of at least one tissue, the method comprises operating a processor to:

apply a developed feature extractor to the image patch to identify one or more tissue segments within the image patch;

apply a developed feature classifier to the one or more tissue segments to identify a respective tissue type and generate a corresponding confidence score representing a degree of similarity according to at least one prediction model generated based on a set of training image patches of a normal tissue of that tissue type, the tissue type being identified according to a hierarchical histology taxonomy;

generate a class activation map for each identified tissue type based on the associated confidence score;

apply pixel-level segmentation to the class activation map to define a contour of each tissue segment of that tissue type to generate the pixel-level segmented image patch;

generate one or more binary masks for the image patch, each binary mask being associated with an identified tissue type and corresponding to a pixel-level representation of one or more tissue segments of that tissue type;

for each binary mask, identify one or more features related to a structure of each tissue segment;

generate one or more feature correspondence values relating each feature identified in each binary mask and each tissue type identified for the image patch; and generate the encoded image patch based on the one or more feature correspondence values.

31. The method of claim 30 comprises operating the processor to generate the feature correspondence value to represent a similarity of a structure of a tissue segment to a feature of the one or more features.

32. The method of claim 30, wherein the encoded image patch comprises a matrix of the one or more feature correspondence values with a number of columns corresponding to a number of unique features identified in the one or more binary masks and a number of rows corresponding to a number of unique tissue types identified for the image patch.

33. The method of claim 30 comprises operating the processor to generate a unique encoded image patch for each hierarchy level of the hierarchical histological taxonomy based on which the one or more tissue types are identified.

34. The method of claim 33 comprises operating the processor to aggregate each unique encoded image patch to generate an aggregated encoded image patch.

35. A system for searching for one or more histopathological images, the system comprises:
    a histopathological image databank constructed using the system of claim 25; and
    a processor operable to:
        receive a search query defining one or more histopathological characteristics; and
        conduct a search of the histopathological databank for one or more encoded image patches that satisfies the search query.

36. A method for searching for one or more histopathological images, the method comprises operating a processor to:
    construct a histopathological image databank according to the method defined in claim 30;
    receive a search query defining one or more histopathological characteristics; and
    conduct a search of the histopathological databank for one or more encoded image patches that satisfies the search query.

* * * * *

UNITED STATES PATENT AND TRADEMARK OFFICE
CERTIFICATE OF CORRECTION

| | |
|---|---|
| PATENT NO. | : 11,636,599 B2 |
| APPLICATION NO. | : 17/944330 |
| DATED | : April 25, 2023 |
| INVENTOR(S) | : Hosseini et al. |

It is certified that error appears in the above-identified patent and that said Letters Patent is hereby corrected as shown below:

In the Specification

Column 13, Line 1:
"dearly"
Should read:
-- clearly --

Column 17, Line 58:
"dump"
Should read:
-- clump --

In the Claims

Claim 8, Column 32, Line 16:
"The system of any claim 1"
Should read:
-- The system of claim 1 --

Claim 28, Column 34, Line 42:
"The system of 25"
Should read:
-- The system of claim 25 --

Signed and Sealed this
Fourth Day of July, 2023

Katherine Kelly Vidal
*Director of the United States Patent and Trademark Office*